(12) United States Patent
Tuan et al.

(10) Patent No.: US 10,900,023 B2
(45) Date of Patent: Jan. 26, 2021

(54) MODULAR, MICROFLUIDIC, MECHANICALLY ACTIVE BIOREACTOR FOR 3D, MULTI-TISSUE, TISSUE CULTURE

(71) Applicants: Rocky S. Tuan, Pittsburgh, PA (US); Hang Lin, Pittsburgh, PA (US); Thomas P. Lozito, Pittsburgh, PA (US); Peter Alexander, Wexford, PA (US); Douglas A. Nelson, Jr., Pittsburgh, PA (US); Riccardo Gottardi, Pittsburgh, PA (US)

(72) Inventors: Rocky S. Tuan, Pittsburgh, PA (US); Hang Lin, Pittsburgh, PA (US); Thomas P. Lozito, Pittsburgh, PA (US); Peter Alexander, Wexford, PA (US); Douglas A. Nelson, Jr., Pittsburgh, PA (US); Riccardo Gottardi, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 636 days.

(21) Appl. No.: 14/913,063

(22) PCT Filed: Aug. 22, 2014

(86) PCT No.: PCT/US2014/052348
§ 371 (c)(1),
(2) Date: Feb. 19, 2016

(87) PCT Pub. No.: WO2015/027186
PCT Pub. Date: Feb. 26, 2015

(65) Prior Publication Data
US 2016/0201037 A1 Jul. 14, 2016

Related U.S. Application Data

(60) Provisional application No. 61/868,979, filed on Aug. 22, 2013.

(51) Int. Cl.
*C12N 5/071* (2010.01)
*C12N 15/90* (2006.01)
(Continued)

(52) U.S. Cl.
CPC ........... *C12N 5/0697* (2013.01); *C12M 21/08* (2013.01); *C12M 23/12* (2013.01); *C12M 23/16* (2013.01);
(Continued)

(58) Field of Classification Search
CPC ...... C12M 21/08; C12M 23/12; C12M 23/16; C12M 23/34; C12M 35/04; C12M 35/08;
(Continued)

(56) References Cited

U.S. PATENT DOCUMENTS 3,361,839 A * 1/1968 Lester .................... B01J 8/0207
585/403
5,011,472 A * 4/1991 Aebischer ............... A61F 2/022
604/153
(Continued)

FOREIGN PATENT DOCUMENTS

WO    WO 2005/047466    5/2005
WO    WO 2007/008609    1/2007
(Continued)

OTHER PUBLICATIONS

International Search Report and Written Opinion for related International Application No. PCT/US2014/052348, dated Dec. 15, 2014, 13 pages.
(Continued)

*Primary Examiner* — Gautam Prakash
*Assistant Examiner* — Lydia Edwards
(74) *Attorney, Agent, or Firm* — Klarquist Sparkman, LLP

(57) ABSTRACT

Disclosed herein are various bioreactor devices and systems for growing cellular material, and related methods of grow-
(Continued)

ing cellular material. In some cases, a system can include a well plate having a plurality of wells and a bioreactor situated in each well of the well plate. In some cases, a bioreactor can include an inner body which divides the bioreactor into several distinct chambers and facilitates the growth of a multi-tissue sample in the bioreactor. In some cases, a system can include a mechanical actuator situated to mechanically stress tissues grown in a bioreactor.

20 Claims, 20 Drawing Sheets

(51) Int. Cl.
  *C12M 1/32* (2006.01)
  *C12M 3/06* (2006.01)
  *C12M 1/00* (2006.01)
  *C12M 3/00* (2006.01)
  *C12M 1/42* (2006.01)

(52) U.S. Cl.
  CPC ............ *C12M 23/34* (2013.01); *C12M 35/04* (2013.01); *C12M 35/08* (2013.01); *C12N 2502/1311* (2013.01); *C12N 2502/1317* (2013.01)

(58) Field of Classification Search
  CPC .... C12N 2502/1311; C12N 2502/1317; C12N 5/0697
  See application file for complete search history.

(56) References Cited

U.S. PATENT DOCUMENTS

| | | |
|---|---|---|
| 5,081,035 A | 1/1992 | Halberstadt et al. |
| D658,306 S | 4/2012 | Gevaert et al. |
| 2002/0028504 A1 | 3/2002 | MacCaskill et al. |
| 2006/0110822 A1 | 5/2006 | Robbins et al. |
| 2007/0128715 A1 | 6/2007 | Vukasinovic et al. |
| 2011/0207175 A1 | 8/2011 | Ei-Sabban et al. |
| 2012/0122208 A1 | 5/2012 | Fisher et al. |
| 2012/0183987 A1* | 7/2012 | Gevaert ............... C12M 23/34 435/29 |
| 2015/0247112 A1 | 9/2015 | Orr et al. |
| 2019/0076840 A1 | 3/2019 | Gottardi et al. |

FOREIGN PATENT DOCUMENTS

| | | |
|---|---|---|
| WO | WO 2010/048417 | 4/2010 |
| WO | WO 2011/014674 | 2/2011 |
| WO | WO 2014/127250 | 8/2014 |
| WO | WO 2015/027186 | 2/2015 |

OTHER PUBLICATIONS

Spitters et al., "A Dual Flow Bioreactor with Controlled Mechanical Stimulation for Cartilage Tissue Engineering," *Tissue Engineering: Part C*, 19(10), 10 pages (Aug. 2013).
Extended European Search Report for Application No. 16854326.2, dated Apr. 4, 2019, 6 pages.
International Search Report and Written Opinion for related International Application No. PCT/US2016/055763, dated Dec. 22, 2016, 16 pages.

* cited by examiner

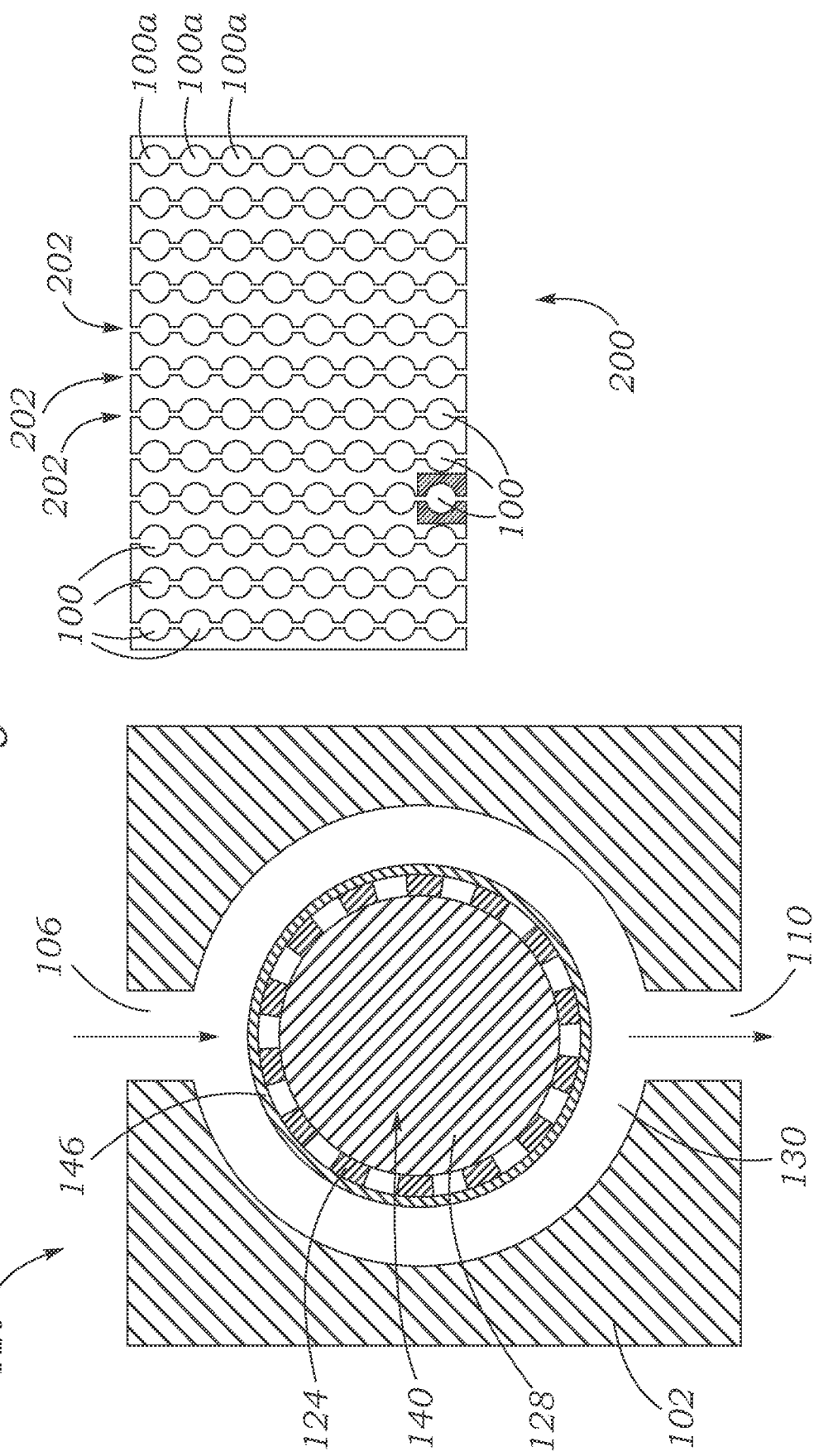

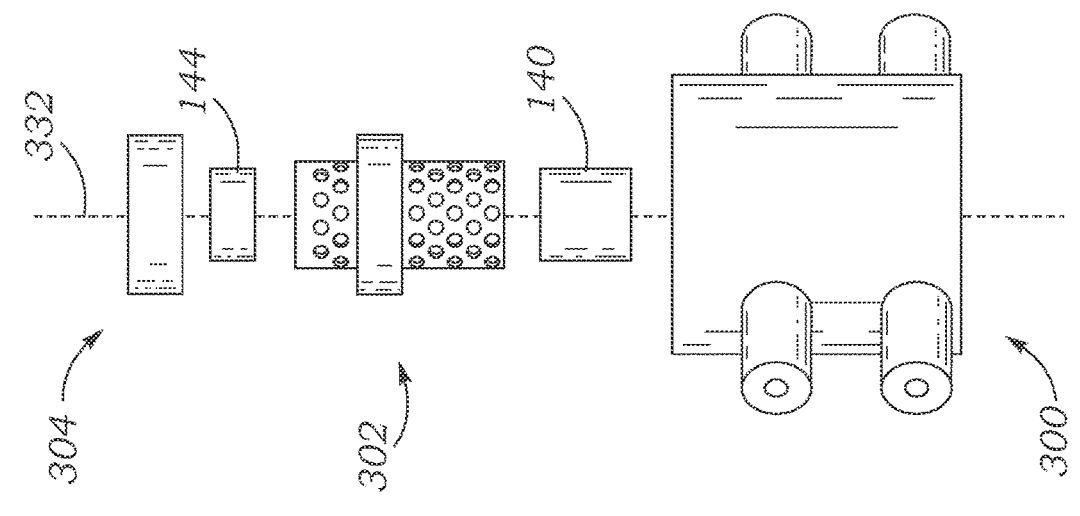
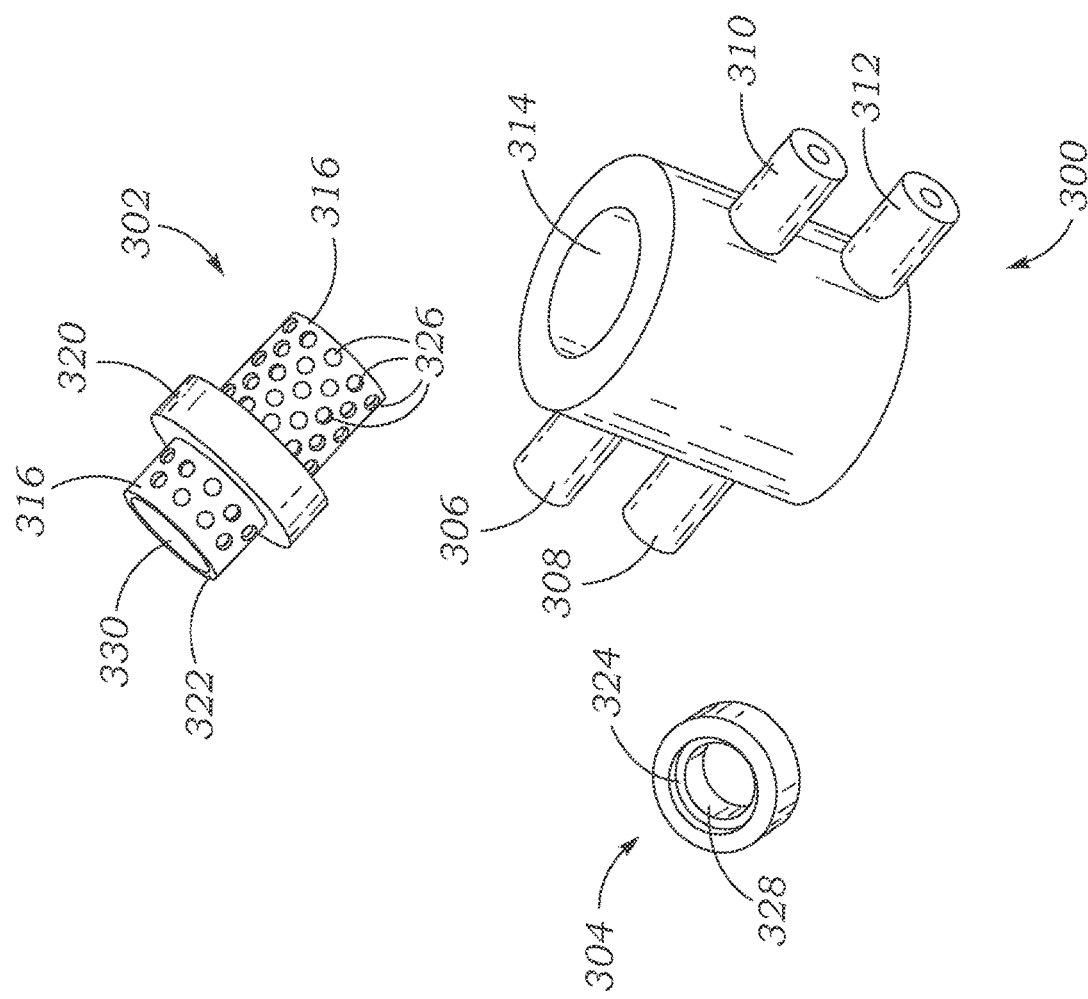

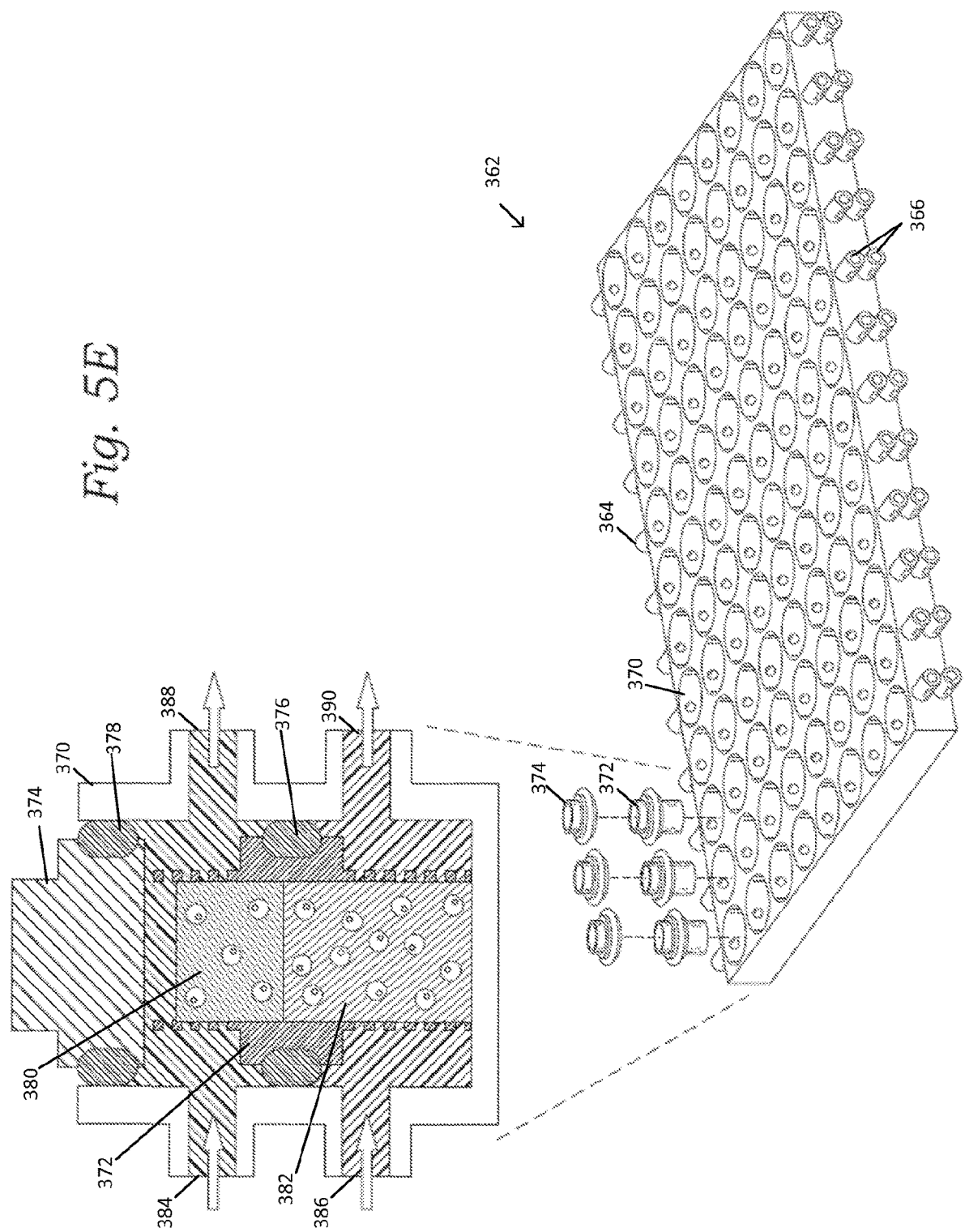

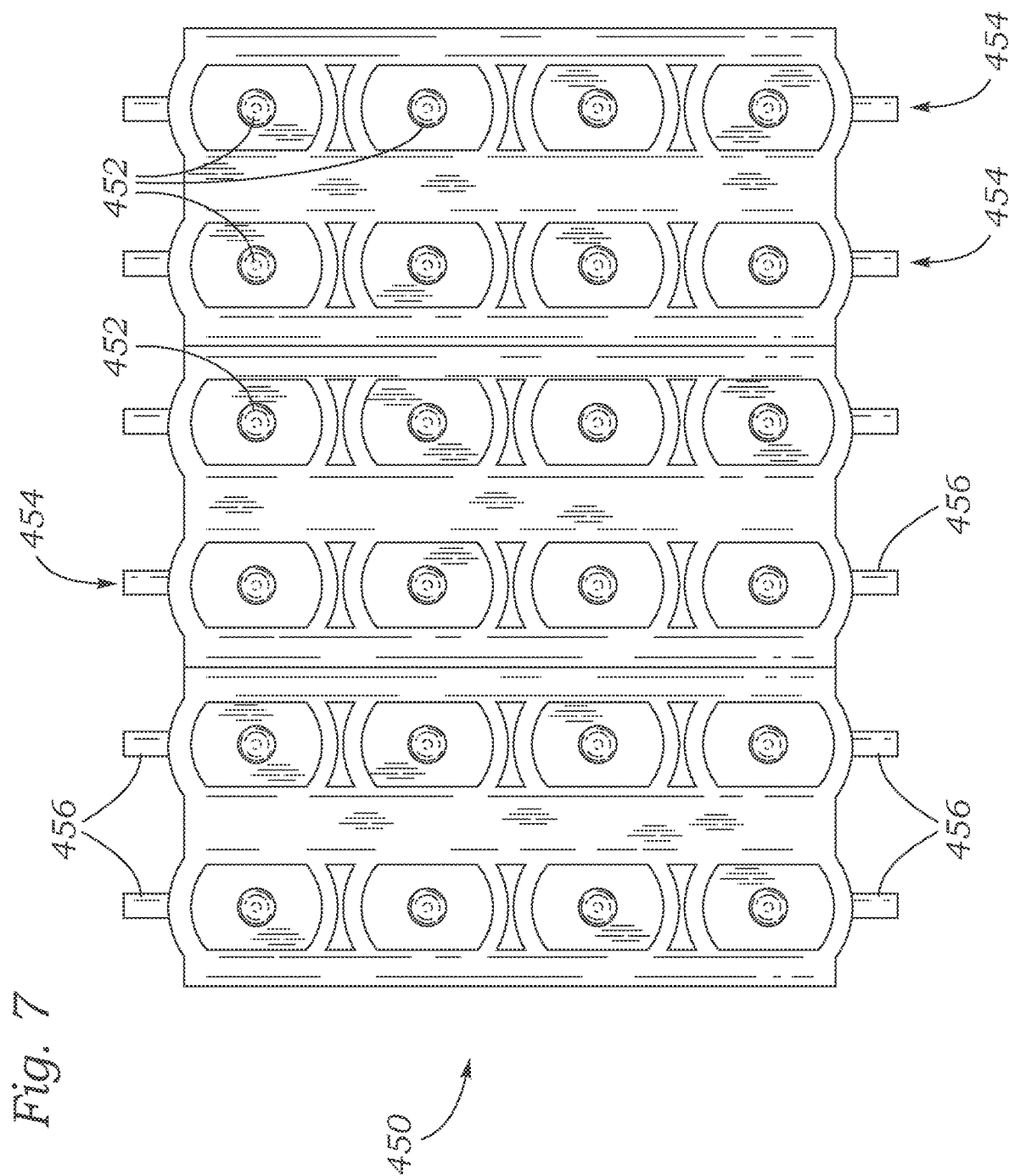

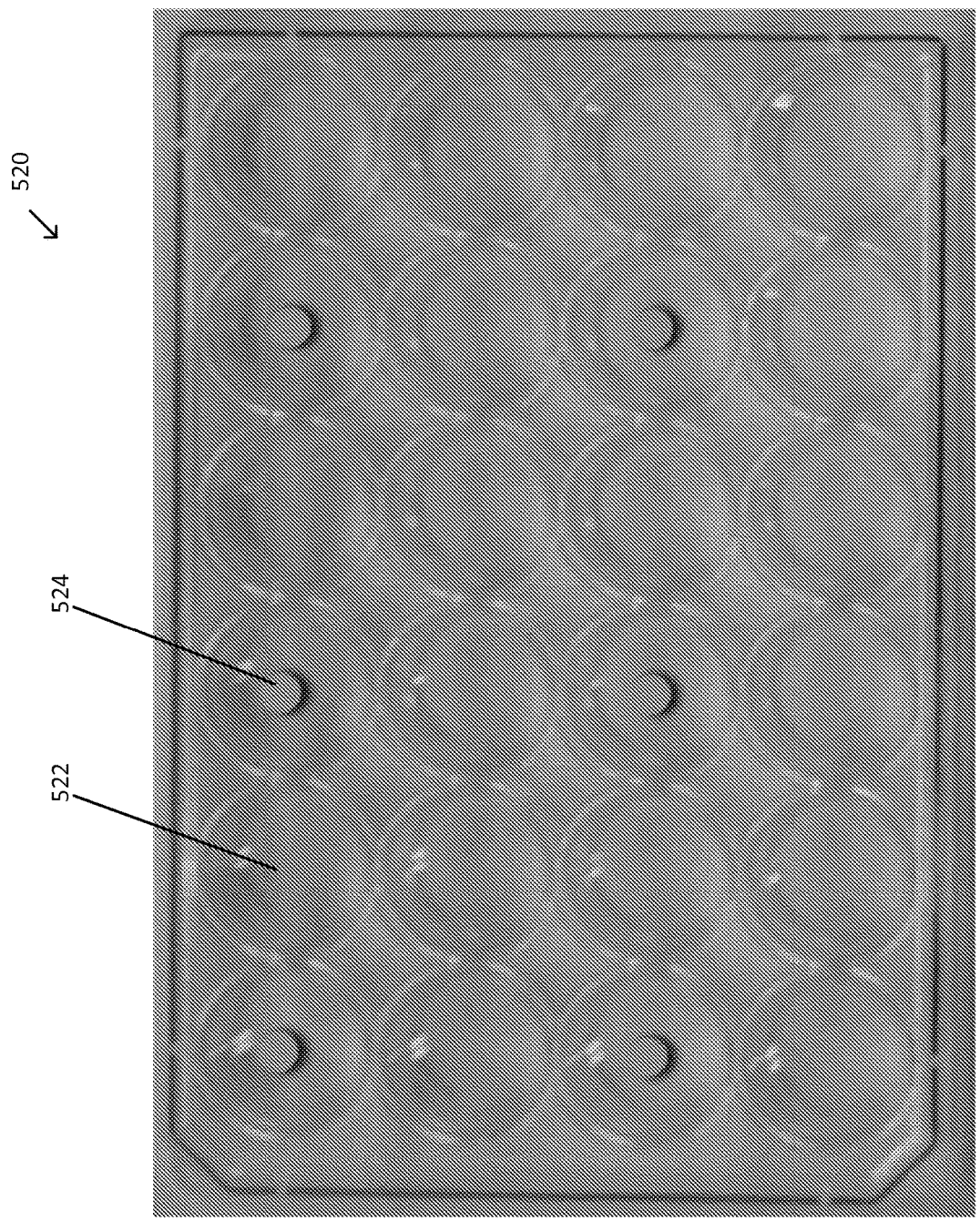

FIG. 12A
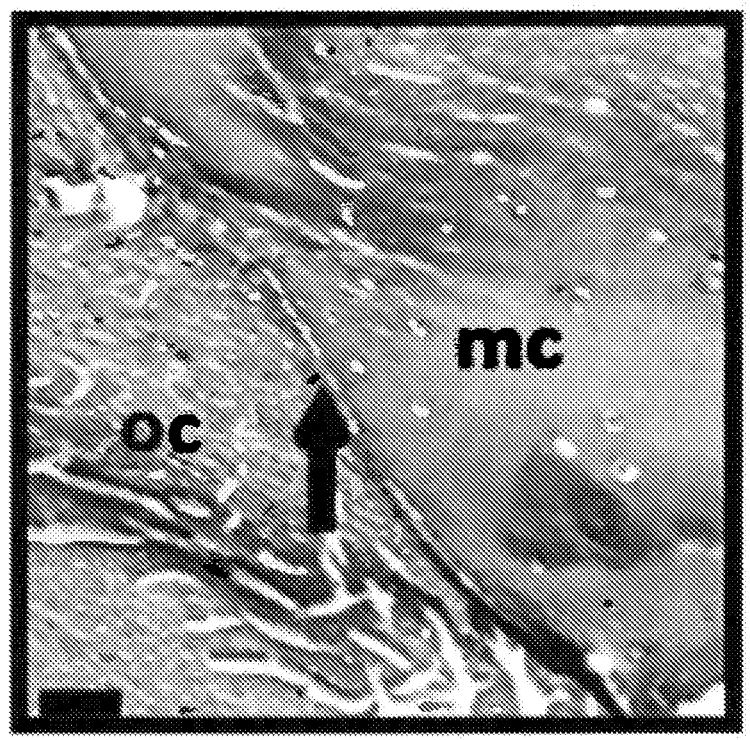
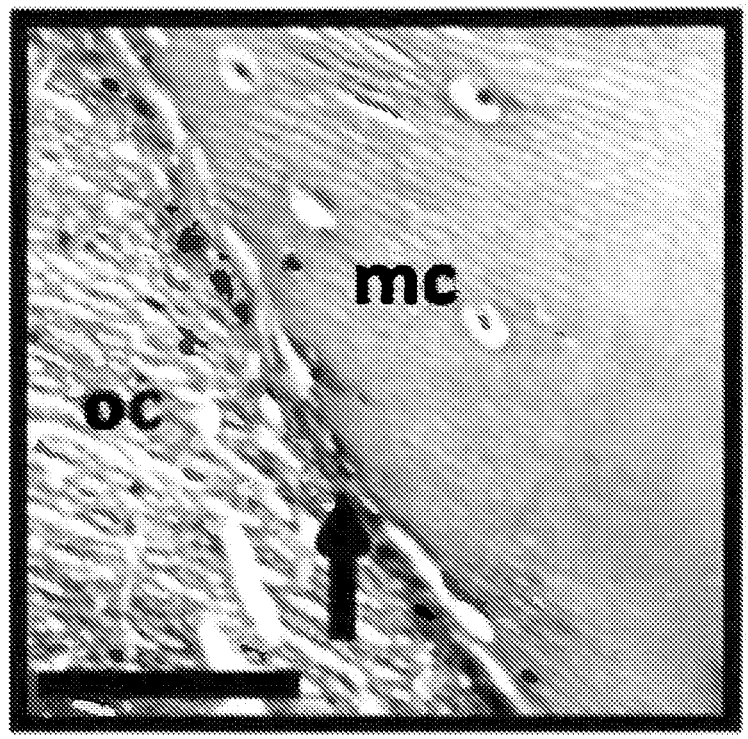
FIG. 12B

FIG. 13A
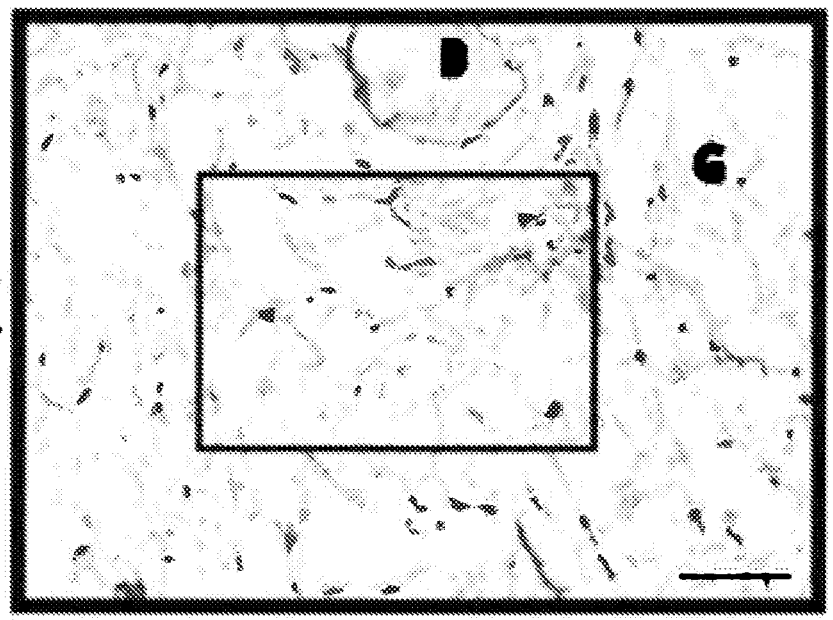
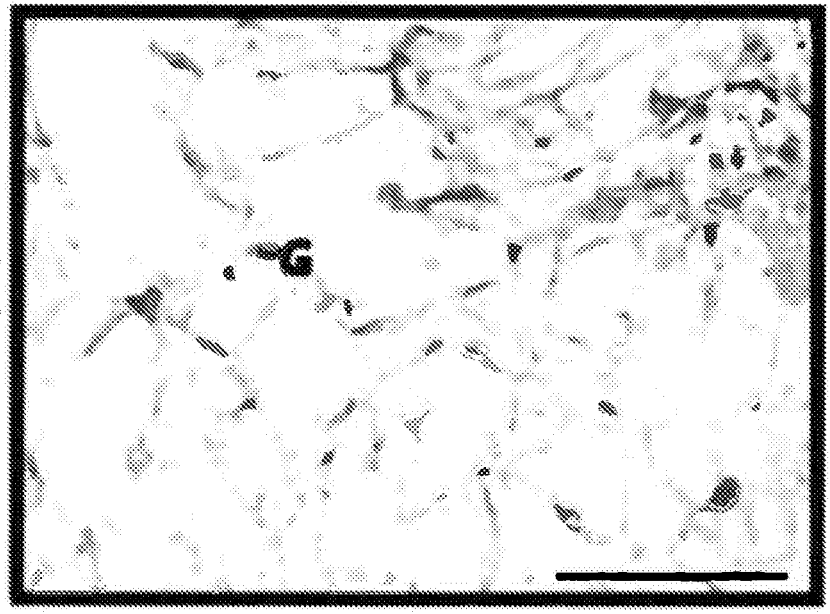
FIG. 13B

FIG. 14A
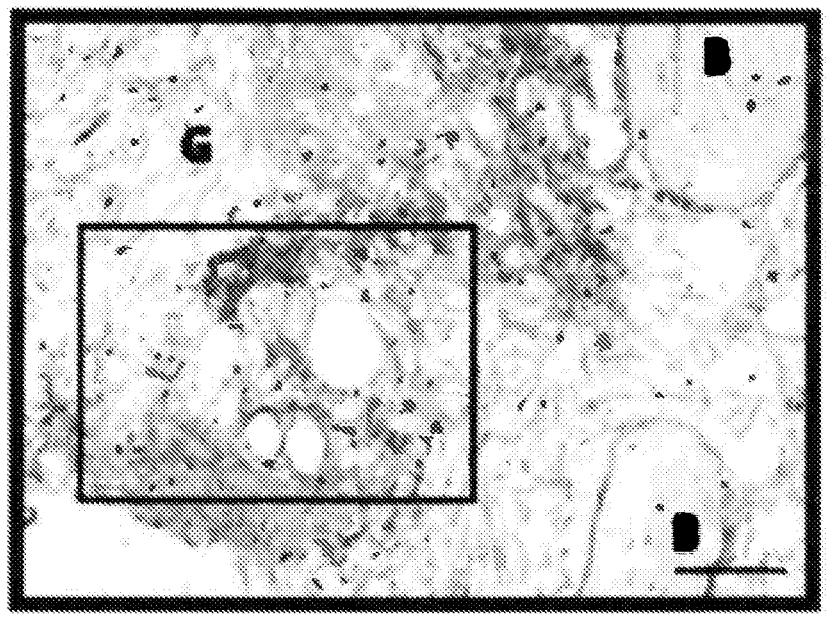
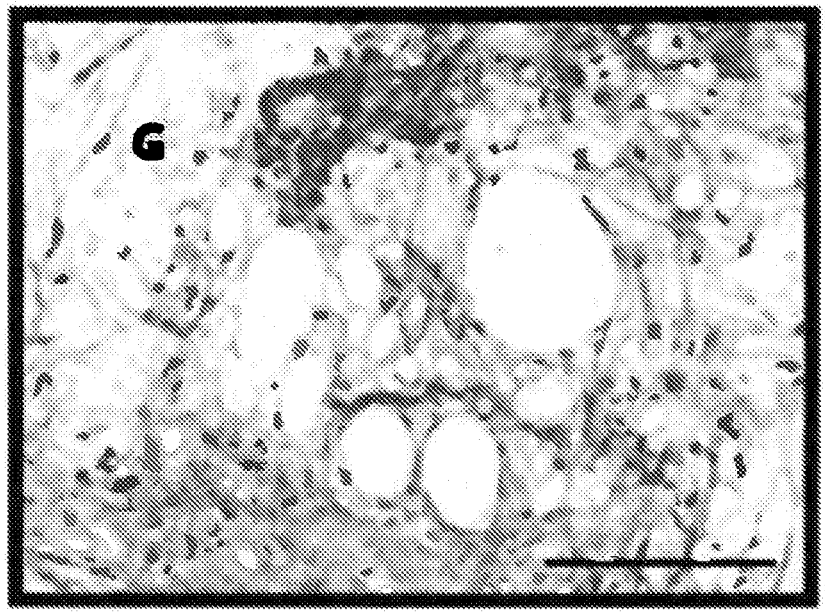
FIG. 14B

MODULAR, MICROFLUIDIC, MECHANICALLY ACTIVE BIOREACTOR FOR 3D, MULTI-TISSUE, TISSUE CULTURE

This application is the U.S. National Stage of International Application No. PCT/US2014/052348, filed Aug. 22, 2014, which was published in English under PCT Article 21(2), and which claims the benefit of U.S. Provisional Patent Application No. 61/868,979, filed Aug. 22, 2013, entitled "A MODULAR, MICROFLUIDIC, MECHANICALLY ACTIVE BIOREACTOR FOR 3D, MULTI-TISSUE, TISSUE CULTURE," which is incorporated by reference herein in its entirety.

ACKNOWLEDGMENT OF GOVERNMENT SUPPORT

This invention was made with government support under Grant No. TR000532 awarded by National Institutes of Health, and Grant No. SAP 4100050913 awarded by the Commonwealth of Pennsylvania Department of Health. The government has certain rights in the invention.

FIELD

The present disclosure relates to the design of bioreactor devices and systems for growing cellular material, and to related methods of growing cellular material.

BACKGROUND

There exist many biological structures comprising multiple layers of different, interacting, tissue types. For example, epithelial layers rest on basement membranes that separate them from different underlying tissue layers, as in the circulatory system (blood vessels), digestive system (esophagus, stomach, intestine), endocrine system (thyroid and other glands), integumentary system (skin), reproductive system (ovaries, fallopian tubes, endometrium, cervix, vagina, testes, and vas deferens), respiratory system (oropharynx, larynx, trachea, bronchioles), sensory system (cornea), and the urinary system (bladder and urethra). Both epithelial and non-epithelial tissues are juxtaposed with different types of biological tissues in the body, and may have cooperative biological effects on one another. It would be helpful to study different tissue types in vitro in an environment that takes into account the interactive nature of biological tissues.

One example of a tissue complex comprising a plurality of different tissues is the osteochondral tissue complex, which can in some cases be affected by osteoarthritis (OA). OA is the most prevalent form of arthritis, affecting up to 15% of the adult population. OA is principally characterized by degeneration of the articular cartilage component of the joint, often with accompanying subchondral bone lesions. Understanding the mechanisms underlying the pathogenesis of OA is important for the rational development of disease modifying OA drugs (DMOADs). Most studies on OA have focused on the investigation of either the cartilage or the bone component of the articular joint.

OA is a chronic degenerative disease of the articular joint which involves cartilage, synovium, ligaments, bone, meniscus, tendon, and peri-articular muscle. Cartilage destruction is one of the common characteristics of OA progression, and results in malfunction of the affected joint. Normal articular cartilage is comprised of large amounts of extracellular matrix (mainly collagen type II), produced and maintained by chondrocytes, the sole cell type in the cartilage. During disease progression, net loss of cartilage matrix results from an imbalance between cartilage matrix degradation and synthesis by chondrocytes in the cartilage. Due to absence of vascularization in the articular cartilage, the capacity of self-repair in cartilage is limited, and currently, there is no effective therapy for the treatment of OA except relieving the symptoms of the diseases until the joints need to be replaced by surgery.

OA involves more than simply degeneration of the articular cartilage—it is in fact a disease of the osteochondral tissue complex. The osteochondral junction is highly structured; the uppermost superficial zone is characterized by elongated chondrocytes with collagen fibrils aligning parallel to the articular surface. In the middle/intermediate zone, rounded chondrocytes and collagen fibrils are less organized relative to the surface. In the deep zone, vertical columns of chondrocytes and fibers are organized perpendicular to the articular surface. The highest concentration of proteoglycans is found in the deep zone. Adjacent to deep cartilage is the calcified cartilage zone, which is characterized by larger and more dispersed hypertrophic chondrocytes. A wavy basophilic matrix, known as the tidemark, highlights the boundary between the deep and calcified cartilage zones. Vertically oriented collagen fibers pass through the tidemark from the deep zone to the calcified cartilage and are important for transferring mechanical forces. Overall, the calcified zone marks the transition from soft cartilage to stiff subchondral bones and is important for attaching the noncalcified cartilage to bone. The subchondral bone is interdigitated with calcified cartilage, but, interestingly, the collagen fibers do not extend from the calcified zone to the bone. This physical linkage between cartilage and bone is a critical component in the pathogenesis of degenerative diseases such as OA.

There exists some debate as to whether OA begins in the cartilage or the bone and whether subchondral bone or articular cartilage is the more appropriate target for disease modifying OA drug (DMOAD) development. Supporters of the "bone first" side of the debate maintain that, as the "substrate" for articular cartilage, subchondral bone plays a support role in cartilage health, and that any perturbations to subchondral bone are amplified as pathological conditions and are transferred from bone to cartilage. For example, studies have shown that osteophyte formation and changes in subchondral bones appear before measurable changes in articular cartilage thickness as well as related joint space narrowing. Another group of studies suggest that healthy subchondral bone is essential for healthy cartilage. In tissue plugs cultured in vitro, bone tissue preserves chondrocyte survival. To some extent, the conventional wisdom has been that healthy subchondral bone presents an impenetrable, impermeable barrier. However, it is possible that cartilage receives nutrients, cytokines, hormones, and other biological signals from bone in vivo, and vice versa.

Proponents of the "cartilage first theory" argue that, while early changes to cartilage during OA are clearly coupled to bone alterations via mechanical and soluble factors, changes to the bone seem to be secondary to alterations in articular cartilage. Supporting evidence suggests that OA changes to cartilage alter the mechanical environment of the bone cells and induce them, in turn, to modulate tissue structure. Several studies report that thickening of calcified cartilage along with tidemark advancement contributes to thinning of articular cartilage. This leads to increased mechanical stresses in the matrix of the deep zone of cartilage and contributes to OA cartilage deterioration.

SUMMARY

The present disclosure describes the construction of an in vitro 3-dimensional (3D) microsystem that models the structure and biology of tissues that are adjacent or contiguous in the body such as the osteochondral complex of the articular joint. In certain embodiments, two or more different tissues can be grown adjacent to one another in a bioreactor. A bioreactor can be configured with at least two chambers, each independently provided with nutrients and/or fluids, such that different tissues grown in the bioreactor can be fed with different nutrients or fluids. Thus, two or more tissues can be grown adjacent to one another and their interaction(s) can be studied.

In certain embodiments, a bioreactor can include an upper chamber having inlet and outlet ports and a lower chamber having inlet and outlet ports. The inlet ports can be fed by the same or independent sources of biological nutrients, such as liquid cell growth medium, that is perfused through each chamber from the inlet port to the outlet port. A first tissue can be situated in the upper chamber so as to be exposed to the biological nutrients fed through the upper inlet port, and a second tissue can be situated in the lower chamber so as to be exposed to the biological nutrients fed through the lower inlet port. In certain embodiments, one or more additional tissue layers can be situated at an interface that extends partially or completely between the first and second tissues. For example, the additional tissue layer may be a stem cell layer that can differentiate into the first tissue and/or the second layer, and/or that mediates biochemical communication between those layers. In particular examples, the additional layer is a stem cell layer of ectoderm, mesenchyme, or endoderm. In some embodiments, the upper chamber and second chamber can establish substantially separate microenvironments for the first and second tissue by supplying separate media or nutrient flow through the upper and lower inlet ports. Biochemical communication between the separate microenvironments can occur via biochemical signals produced by the additional intermediate layer at the interface instead of via the nutrient media flow.

One exemplary application of the devices, systems and methods described herein is in improved studies of the osteochondral complex and OA. While previous OA studies have focused on the investigation of either the cartilage or the bone component of the articular joint, the osteochondral complex represents a more physiologically relevant target as OA ultimately is a disorder of osteochondral integrity and function. Thus, interactions between both bone and cartilage are central to OA progression, and in studying OA, bone and cartilage are capable of being studied together instead of separately. Thus, the present disclosure describes 3D microtissue constructs including both cartilage and bone, in order to appropriately study the osteochondral environment and OA in vitro.

Different osteogenic and chondrogenic tissue components can be produced using adult human mesenchymal stem cells (MSCs) derived from bone marrow and adipose seeded within biomaterial scaffolds photostereolithographically fabricated with a well-defined internal architecture. A 3D perfusion-ready container platform, such as a 3D printed platform, can house and maintain an osteochondral microsystem having any combination or all of the following features: (1) an anatomic cartilage/bone biphasic structure with a functional interface; (2) all tissue components derived from a single stem cell, such as an adult mesenchymal stem cell source to eliminate possible age/tissue type incompatibility; (3) individual compartments to constitute separate microenvironments, for example for the "synovial" and "osseous" components; (4) accessible individual compartments which can be controlled and regulated via the introduction of bioactive agents or candidate effector cells, and tissue/medium sampling and compositional assays; and (5) compatibility with the application of mechanical load or other perturbations, such as chemical, toxicological and other physical perturbations. In certain embodiments, the container platform is dimensioned to fit within the wells of multiwell tissue culture plates, such as 24, 48, or 96 well plates, to perform high-throughput assays. The bioreactor can also have remote imaging capability to allow non-invasive functional monitoring of the bioreactor tissues.

The consequences of external perturbations, such as mechanical injury, exposure to drugs or inflammatory cytokines, and compromised bone quality, on degenerative changes in the cartilage component can be examined in the osteochondral microsystem as a first step towards its eventual application as an improved and high-throughput in vitro model for prediction of efficacy, safety, bioavailability, and toxicology outcomes for candidate DMOADs. For example, the effect of corticosteroids or osteoactive agents on the different tissue types, such as bone and cartilage tissue, can be assessed. In addition, drug screening can be performed to identify potential therapeutic agents to treat OA.

In some embodiments, a bioreactor can include a fluidic well plate having dimensions equivalent to those of standard laboratory multi-well plates. The fluidic well plate can have various numbers of wells, such as one well, six wells, twelve wells, twenty-four wells, or ninety-six wells. The wells of the well plates can be arranged in a grid having rows and columns, and a row or a column of wells can be fluidically connected by a first conduit feeding upper portions of each of the wells in the row or column and by a second conduit feeding lower portions of each of the wells in the row or column Each conduit can begin and terminate at the end of the plate at an inlet or an outlet port.

In some embodiments, a bioreactor can include a fluidic well insert configured to fit tightly within one of the wells of the fluidic well plate and to support biological tissues at an interior of the insert. The insert can include a circumferential flange which seals the insert against the inside surface of one of the wells of the fluidic well plate, thereby separating the respective well into the upper and lower portions fed by the first and second conduits, respectively. The insert can be hollow and thus biological tissues can be housed inside the insert. The circumferential flange can separate an upper portion of the insert from a lower portion of the insert, and each of the upper and lower portions of the insert can include pores through which fluids can flow. The insert can be configured to be situated within a standardized, commercially available well plate.

In some embodiments, a bioreactor can include a lid and an associated support system which is configured to seal the fluidic well plate. The lid can include a micro-mechanical actuator and a force sensor to provide controllable deformation or load to tissue constructs in the well plate. The micromechanical actuator can be associated with and aligned on center with a well of the well plate. The lid can be used with a commercially available well plate with or without an insert situated in a well thereof.

Some embodiments include a modular, microfluidic, multi-tissue, mechano-active 3D bioreactor. A bioreactor can include a microfluidic base, a bioreactor insert, and a mechanoactivating lid assembly. In various embodiments, a base, insert, and lid assembly can be used in various combinations, sub-combinations, or individually. In some embodiments, a base permits direct or indirect interaction of two or more native or engineered tissue types while simultaneously providing separate fluid types to the various tissue types via microfluidic conduits which feed the tissue directly or via biological or physical intermediates within the geometry of standard multi-well plates.

A bioreactor can be amenable and adaptable to common tissue culture practices and devices (e.g., multi-channel pipettes, etc.) and high-throughput formats, depending on the scale of the wells. The insert can divide a single well into upper and lower compartments which do not communicate directly. They may interact indirectly only through the intervening tissue/construct disposed within an inner chamber. Two or more tissues in the inner chamber can interact with each other directly or indirectly while being exposed to two different environments. The dimensions of the inserts can be adapted to fit tissue culture containers of any size and shape. Tissues grown in a bioreactor can be exposed to mechano-activating or other damaging forces. A mechano-activating lid assembly can load and test tissue along a vertical axis while maintaining sterility of the system.

Some embodiments allow growth of an anatomic biphasic structure with a functional interface, and allow growth of each tissue type from a single cell source to eliminate possible age/tissue type incompatibility. Some embodiments include individual compartments to constitute separate microenvironments for the different tissue types, such as for the "synovial" and "osseous" components of a microtissue, each being independently accessible to allow introduction of bioactive agents or candidate effector cells. Some embodiments are compatible with the application of mechanical load and perturbation, as well as with imaging capability to allow for non-invasive functional monitoring.

The devices, systems, and methods described herein can be used to study bone-cartilage interaction to investigate OA, although their applicability is not so limited. The devices, systems, and methods disclosed herein can be used to study bone-cartilage interaction to investigate other biological processes or effects, or can be used to study the interaction between other types of tissues. The foregoing and other objects, features, and advantages of the invention will become more apparent from the following detailed description, which proceeds with reference to the accompanying figures.

BRIEF DESCRIPTION OF THE DRAWINGS

FIG. 2 shows a schematic, cross-sectional plan view of an exemplary bioreactor, a plan view of an exemplary array of bioreactors, and a location of the exemplary bioreactor in the exemplary array of bioreactors.

FIG. 3 shows three-dimensional renderings of an exemplary shell of a bioreactor, inner body of a bioreactor, and upper ring of a bioreactor, in perspective views.

FIG. 4 shows a three-dimensional rendering of the components of an exemplary bioreactor, in an exploded view.

FIG. 5E is a schematic representation of a multiwell, dual chamber bioreactor system, with a 96 well bioreactor platform shown on the right, and a cross-sectional view of a single bioreactor on the left.

FIG. 7 shows an image of an exemplary array of 24 bioreactors, from a top plan view.

FIG. 8A illustrates an exemplary method of imparting an array of bioreactors with loading forces in groups of six at a time.

FIGS. 12A and 12B show histology images of exemplary tissues grown according to the techniques described herein, at 10× and 20× magnification, respectively.

FIGS. 13A and 13B show osteoprotegerin IHC images of tissues grown in the absence of endothelial cells, at 10× and 20× magnification, respectively.

FIGS. 14A and 14B show osteoprotegerin IHC images of tissues grown in the presence of endothelial cells, at 10× and 20× magnification, respectively.

DETAILED DESCRIPTION

Figure 1:
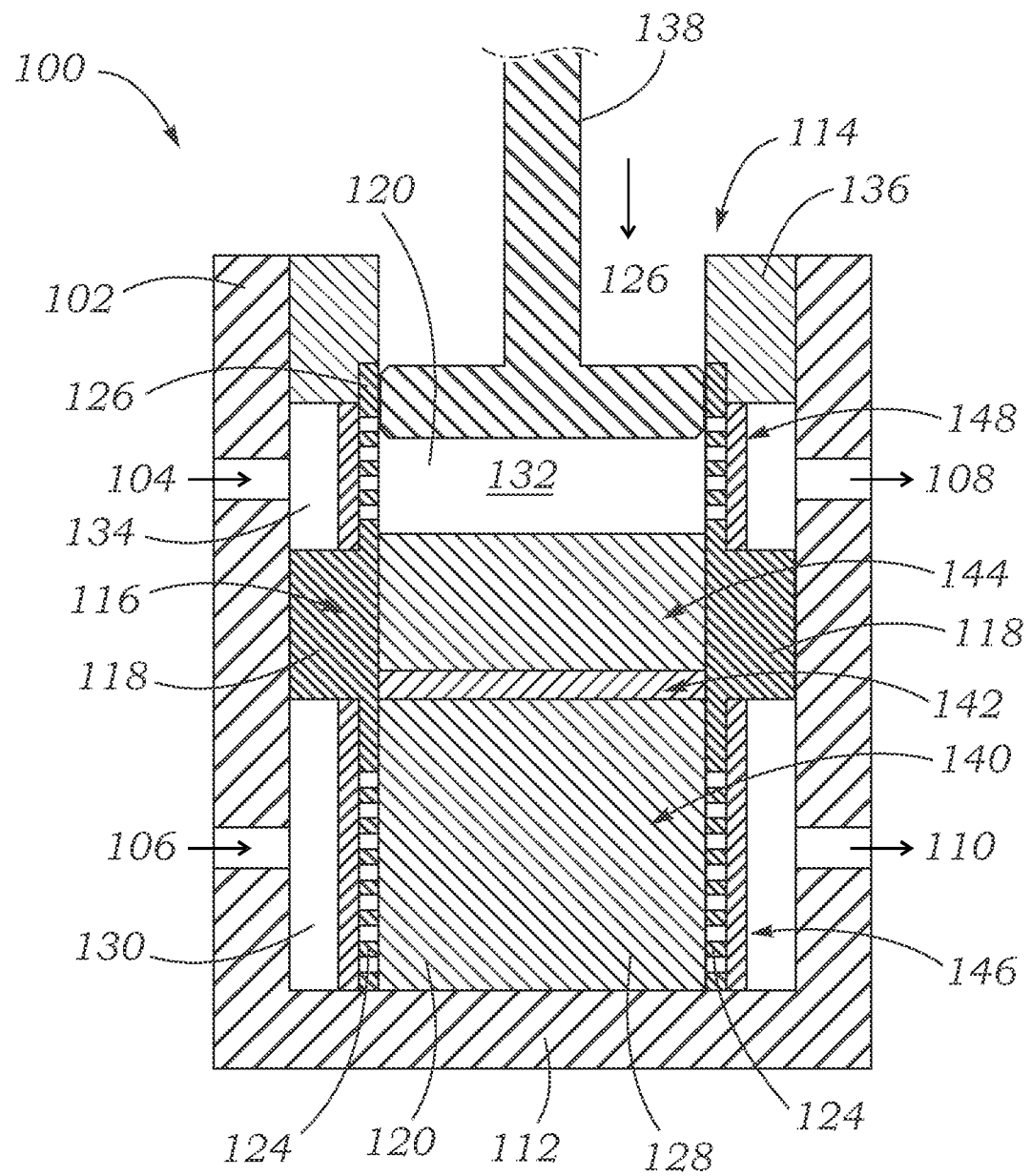
FIG. 1 shows a schematic, cross-sectional side view of an exemplary bioreactor having a microsystem of plural different tissue types growing therein.

As used herein, "tissue" refers to an aggregation of one or more types of specialized cells united in the performance of a particular function. Organs are formed by the functional groupings of multiple component tissues, hence the tissue may be different types of cells from a particular organ, such as bone. Different tissues can be divided into different categories in several ways, such as based on the embryonic origin of the tissue from ectoderm, mesoderm, or endoderm. Alternatively, the tissue may be a subunit of a physiological system, for example, bone and cartilage in the skeletal system, or an organ, such as dermis and epidermis in the skin, parenchyma and capsule in the liver, sinusoids and parenchyma in the liver, intestinal epithelium and underlying mucosa in the intestine, neurons and myelin in a peripheral nerve, corneal endothelium and epithelium in the eye, renal cortex and medulla in the kidney, and a variety of other distinct but anatomically adjacent tissues that may be found in the body. However, the different tissue types are not confined to normal anatomic tissues but can also include different types of specialized cells found in pathological conditions, such as tumor and adjacent non-tumor tissue of the same or different type, such as adenocarcinoma of the breast and adjacent normal (non-malignant) breast tissue.

As used herein, "chondrocyte" refers to cells found in healthy cartilage, which help to produce and maintain the cartilaginous matrix. As used herein, "osteoblast" refers to the cells responsible for bone formation, which produce and mineralize a matrix of osteoid. A tissue that comprises chondrocytes or osteoblasts is a tissue that contains them, but need not exclusively consist of them. Examples of a tissue that comprises chondrocytes are native cartilage or a culture of chondrocytes as in an artificial cartilage construct. Examples of a tissue that comprises osteoblasts is native bone or a culture of osteoblasts as in an artificial osteoblast construct. As used herein, "matrix" refers to any material disposed between cells. A "matrix" can include any of various suitable biological or synthetic materials. As used herein, "gel" refers to a solid, jelly-like material having a substantially dilute cross-linked structure exhibiting no flow when in the steady state. As used herein, "nutrient" refers to a biological substrate (such as a chemical, vitamin, blood serum, salt, yeast extract, etc.) that a cell requires to live, grow, and/or function, which must be or is advantageously taken from its environment. Examples of other types of nutrients are various carbohydrates, fats, proteins, amino acids, minerals, water, oxygen, and various signaling molecules such as cytokines, growth factors, hormones, and metabolites. As used herein, "OA" refers to osteoarthritis. As used herein, "DMOAD" refers to a disease modifying osteoarthritis drug, which is a subset of a disease modifying drug (DMD).

Tissues that are in "functional contact" with each other need not be in physical contact, but can be separated by an intermediate layer that mediates biochemical communication between the tissues. For example, a layer of mesenchymal stem cells between a layer of chondrocytes and osteoblasts can physically separate them but still permit biochemical communication between the chondrocyte and osteoblast layers.

Engineered tissue constructs which properly incorporate plural tissue layers into an interactive microtissue unit can help in accurately studying biological tissues and their interactions, and can help in elucidating the pathogenesis of various diseases and assessing the efficacy of potential therapeutics against those diseases. Some of the devices, systems, and methods described herein facilitate the growth of physiologically accurate microsystems having distinct biological tissue layers, such as those found within an organ (e.g., the liver) or other physiological system (e.g., the skeletal system). Portions of the current disclosure refer to the osteochondral complex and OA, which are of particular interest herein, although the devices, systems, and methods disclosed should be understood to be applicable to multi-tissue cultures generally.

A "nutrient fluid" is a liquid that supplies nutrients to living cells, such as a culture medium. Some such media are specialized to support the growth of a particular type of tissue, such as cartilage (cartilage media) or bone (bone media) or the cells contained in such tissue.

FIG. 1 shows a cross-sectional view of an exemplary bioreactor 100. Bioreactor 100 includes a shell 102 having a generally cylindrical inner space, as well as an upper inlet 104, lower inlet 106, upper outlet 108, and lower outlet 110. The shell 102 has a closed bottom end 112 and an open top end 114. Several components are situated within the shell 102 in order to facilitate desirable cellular growth therein. For example, the shell 102 encloses an inner body 116 which has a hollow interior 120 and includes a central protruding ring 118 having an outer diameter approximating the inner diameter of the shell 102. The inner body 116 also includes a lower porous screen 124, such as having lateral perforations, and an upper porous screen 126, such as having lateral perforations, each of which can have an outside diameter which is smaller than the inside diameter of the shell 102. Together, the protruding ring 118 and porous screens 124, 126 divide the interior of the shell 102 into an inner lower chamber 128, an outer lower chamber 130, an inner upper chamber 132, and an outer upper chamber 134. Fluids can flow laterally through the upper porous screen 126 between the inner upper chamber 132 and the outer upper chamber 134, and fluids can flow laterally through the lower porous screen 124 between the inner lower chamber 128 and the outer lower chamber 130.

As shown in FIG. 1, the bioreactor 100 can further include an upper ring 136 and a piston 138. The piston 138 can be used to impart a compressive force on materials situated within the bioreactor 100, and the upper ring 136 can form a sealing element between the piston 138 and the shell 102. The upper ring 136 seals the open top end 114 of the bioreactor 100 while allowing the piston 138 to move into and out of the shell 102. Various substances (e.g., nutrients) can flow into the bioreactor 100 through the inlets 104, 106, around or through the inner body 116, and out of the bioreactor 100 through the outlets 108, 110.

Some of the substances entering the bioreactor 100 through inlet 104, for example, can flow around the upper porous screen 126 and out the outlet 108. Some of the media entering the bioreactor 100 through inlet 104 (the amount depending on the characteristics of the components of the system) can also flow laterally through the upper porous screen 126, through cellular tissues growing inside the inner body 116, flow laterally through the opposing side of the upper porous screen 126, and out through outlet 108. Finally, some of the media entering the bioreactor 100 through inlet 104 (again, the amount depending on the characteristics of the components of the system) can also flow through the upper porous screen 126, through cellular tissues growing inside the inner body 116, through the lower porous screen 124, and out through outlet 110. Corresponding flow paths are available for media entering the bioreactor through inlet 106.

This design allows for the provision of different fluids, compounds, and nutrients (e.g., a tissue culture medium or nutrient broth such as serum, or various other growth factors, steroids, growth hormones, etc.), or different concentrations of such materials, to the upper and lower chambers, and thus to different biological tissue layers disposed within the bioreactor 100. In some cases, the specific fluids and nutrients used can be tailored to the particular cell types grown in the bioreactor. For example, in bioreactor 100, hypoxic fluids can be fed through the upper chamber while normoxic fluids are fed through the lower chamber.

FIG. 1 shows that cellular material can be grown in at least 5 separate regions within the bioreactor 100. As shown, an osteoblast construct 140 can grow in the inner lower chamber 128, a mesenchymal construct 142 can grow on top of the osteoblast construct 140, and a chondrocyte construct 144 can grow on top of the mesenchymal construct 142. The chondrocyte construct 144 can be exposed to the piston 138 or a layer of synovial fluid can separate the chondrocyte construct 144 from the piston 138, and in either case, the piston 138 can be actuated to impart forces through the chondrocyte construct 144, the mesenchymal construct 142, and the osteoblast construct 140 to the bottom end 112 of the shell 102. Further, a layer of endothelial cells 146 can grow on the exterior of the lower porous screen 124, and a layer of human fibroblast cells 148 can grow on the exterior of the upper porous screen 126.

FIG. 2 shows a cross sectional plan view of the bioreactor 100 and its location within an exemplary array 200 of ninety six bioreactors 100. FIG. 2 shows that plural bioreactors 100 can be arranged in an array 200 such that the outlets of some bioreactors are fluidly coupled to the inlets of other bioreactors. For example, the outlets 108, 110 of bioreactor 100a are coupled to the inlets 104, 106 of bioreactor 100b, respectively, and the outlets 108, 110 of bioreactor 100b are coupled to the inlets 104, 106 of bioreactor 100c, respectively. Thus, a plurality of bioreactors 100 can be coupled in series to facilitate distribution of substances through them. Additionally, a plurality of series 202 of multiple bioreactors 100 can be arranged adjacent one another to form the array 200. The plurality of series 202 can be fluidly coupled either in series or in parallel with one another.

FIG. 3 shows an exemplary shell 300, exemplary inner body 302, and an exemplary upper ring 304. The shell 300 has an overall hollow cylindrical shape, and comprises an upper inlet 306, a lower inlet 308, an upper outlet 310, and a lower outlet 312, each of which comprises a hollow, generally cylindrical extension extending radially outwardly from the shell 300. The shell 300 also includes a hollow, generally cylindrical inner space 314 within which the inner body 302, upper ring 304, and cellular material can be situated. The inner body 302 includes a lower porous screen 318 and an upper porous screen 316, both of which include a plurality of pores, or small openings, 326. The inner body 302 also includes a protruding ring 320 which protrudes radially outwardly from the rest of the inner body 302, and which has an outside diameter approximating the inner diameter of the inner space 314. Thus, when the inner body 302 is situated within the shell 300, several distinct chambers can be formed, as described above with regard to bioreactor 100.

FIG. 3 also shows that upper ring 304 has a groove 324 extending around the circumference of the inner surface of one end of the upper ring 304. The upper ring also has a main inner surface 328 having a generally cylindrical shape and an inner diameter approximating an inner diameter of the inner cylindrical space 330 in the inner body 302. FIG. 4 shows the exemplary shell 300, inner body 302, upper ring 304, chondrocyte construct 144, and osteoblast construct 140, aligned along axis 332 in an exploded view. These elements can be combined, together with a mesenchymal construct (not shown) to form a bioreactor similar to bioreactor 100. When these components are assembled to form a bioreactor in this manner, the osteoblast construct 140, mesenchymal construct, and chondrocyte construct 144 are situated within the inner space 330 within the inner body 302. Further, a top end portion 322 of the inner body 302 can be situated within the groove 324 of the upper ring 304 to facilitate sealing of the system (note a similar structural configuration in FIG. 1—a top end of the upper porous screen 126 is situated within a similar groove at the bottom end portion of the upper sealing ring 136).

Figure 5A:
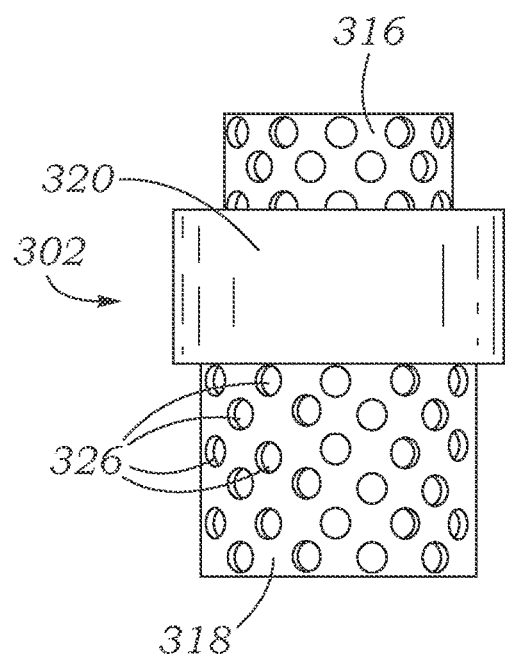
FIGS. 5A-5B show three-dimensional renderings of exemplary inner bodies for use in bioreactor systems, from two different views.
Figure 5B:
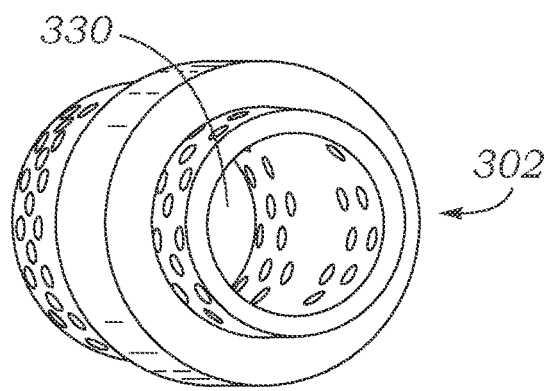
Figure 5C:
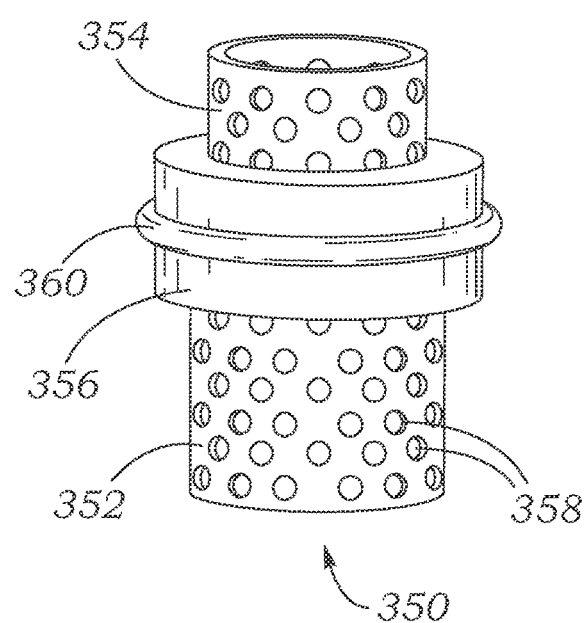
FIGS. 5C-5D show photographs of exemplary inner bodies for use in bioreactor systems, from two different views.
Figure 5D:
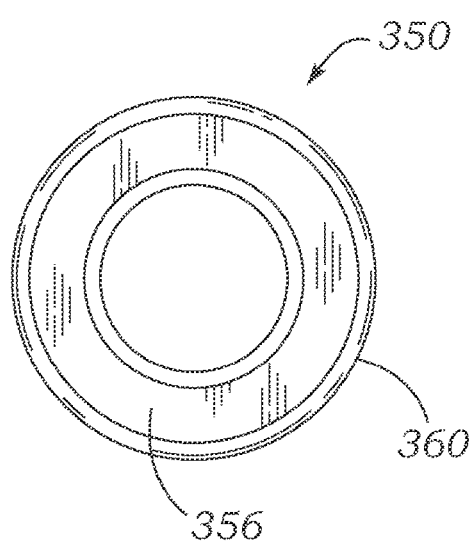

FIGS. 5A-5B show alternate views of the inner body 302 shown in FIGS. 3-4. FIG. 5B shows that the inner body 302 has a cylindrical inner open space 330 which spans through the entire body 302 to accommodate the positioning of cellular material therein. FIGS. 5C-D illustrate an inner body 350 comprising a lower porous screen 352, an upper porous screen 354, and a protruding ring 356. The lower and upper porous screens have a plurality of pores 358. The inner body 350 also includes a sealing o-ring 360 disposed around the outside of the central protruding ring 356. The o-ring 360 helps seal the inner body 350 against the inner surface of a shell (e.g., shell 102) to more effectively maintain distinct chambers within the shell. The inner body 350 can be fabricated, for example, photolithographically using a biocompatible plastic-polymer. In some embodiments, the shell, body and/or ring of an inner body, or other parts of a bioreactor, can be fabricated with commercially available E-shell 300™ polymer resin using photo-stereolithography (PSL).

FIG. 5E is a schematic representation of a multiwell, dual chamber bioreactor system, with a 96 well bioreactor platform 362 shown at the lower right, and a cross-sectional view of a single bioreactor shown at the upper left. The multi-well platform 362 includes a plurality or rows of eight wells 370 that are in fluid communication from one inlet/outlet pair 364 across the row of wells 370 to an opposite inlet/outlet pair 366. Each well 370 is configured to receive a bioreactor insert 372 and a sealing lid 374 (the lid can be replaced with and/or incorporated into a mechanical actuator or piston that applies a mechanical loading pattern downward on the tissue/fluid in the bioreactor). The insert 372 is sealingly engaged with the inner surfaces of the well 370 via an o-ring 376 to form separate upper and lower fluid flow chambers. The lid 374 is also sealingly engaged with the inner surfaces of the well 370 via another o-ring 378 to prevent fluid escaping from the well. The insert 372 can contain at least two layers of biological material, such an upper layer 380 and a lower layer 382 as shown. The upper layer 380 can comprise a chondral construct and/or the lower layer 382 can comprise a osseous construct, for example. One or more additional layers, such as an intermediate layer, can also be included. An intermediate mesenchymal layer can be included, for example. Each well has two opposing upper inlet/outlets 384 and 388, which allow a first fluid to flow through the upper chamber to interact with the upper layer 380, and two opposing lower inlets/outlets 386, 390, which allow a second fluid to flow through the lower chamber to interact with the lower layer 382. The first fluid can comprise a chondrogenic medium and/or the second fluid can comprise an osteogenic medium, for example.

As illustrated in FIG. 5E, the first fluid can enter at 384 and then pass laterally through perforations in the insert 372 to enter the upper layer 380 laterally. The first fluid can then exit the upper layer 380 laterally through the perforations in the insert 372 before exiting the bioreactor at 388. The perforations can extend circumferentially around the insert 372 such that the first fluid can flow around the upper layer and can interact laterally with the upper layer from all lateral sides. Some of the first fluid can also flow over the top of the upper layer and perfuse into and out of the upper layer from its upper surface. Similarly, the second fluid can enter at 386 and then pass laterally through perforations in the lower portion of insert 372 to enter the lower layer 382 laterally. The second fluid can then exit the lower layer 382 laterally through the perforations in the insert 372 before exiting the bioreactor at 390. The perforations can extend circumferentially around the lower portion of the insert 372 such that the second fluid can flow around the lower layer and can interact laterally with the lower layer from all lateral sides.

Figure 6A:
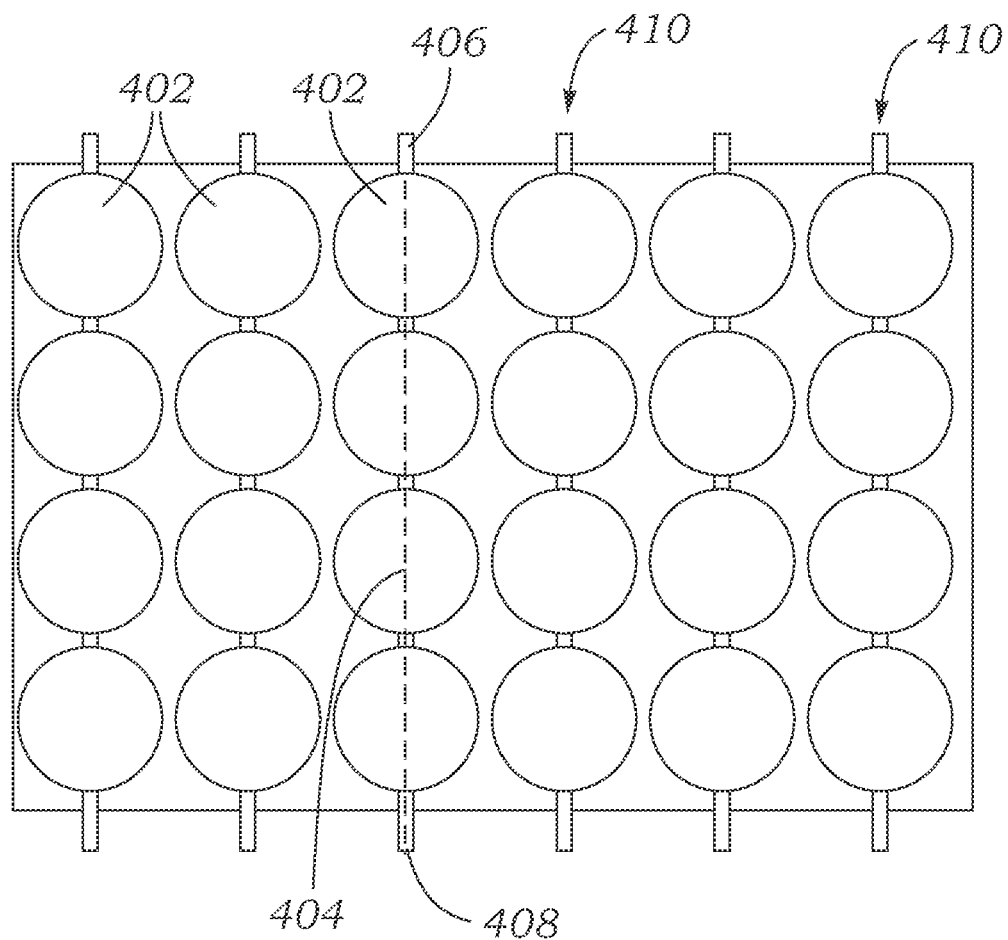
FIG. 6A shows a schematic plan view of an exemplary well plate having an array of wells therein, within each of which a bioreactor inner body can be situated, as well as a plurality of flow paths through the well plate.
Figure 6B:
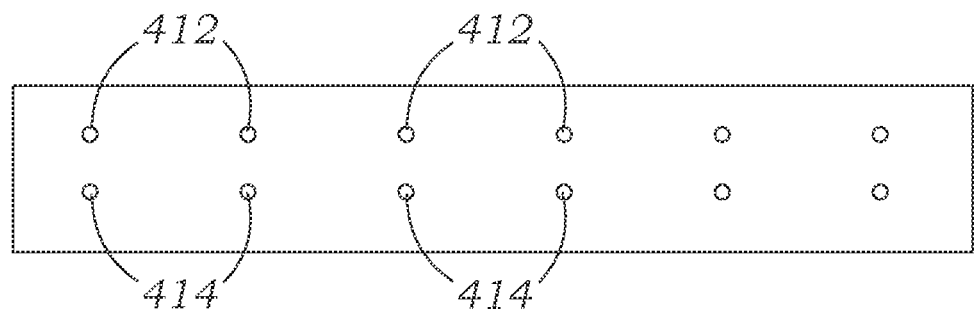
FIG. 6B shows a schematic side view of the well plate of FIG. 6A, including a plurality of upper ports and a plurality of lower ports.

FIG. 6A illustrates in plan view an exemplary array 400 of wells 402, within each of which an insert such as insert 350 can be situated. The array 400 of wells 402 includes six sets 410 of four wells 402 fluidly coupled in series. Thus, a flow path through four wells 402 is illustrated as conduit path 404, along which fluids can flow either from a first end 406 to a second end 408 or from the second end 408 to the first end 406. Thus, the first end 406 can be either an inlet or and outlet, and the second end 408 can be either an inlet or an outlet, depending on the direction of flow along the conduit path 404. FIG. 6B illustrates the array 400 from a side view, showing that each set 410 of wells 402 can have both an upper port 412 and a lower port 414 for carrying fluids into or out of the set 410 of wells 402, depending on the direction of flow along the conduit path 404.

FIG. 7 shows an array 450 of wells 452 similar to the array 400, with twenty-four wells 452 each having an integrated well insert. The wells 452 are arranged in six sets 454 of four wells 452 fluidly coupled in series. Each of the six sets of wells 452 is provided with a port 456 at each end, through which fluid can either enter or exit, depending on the flow path through the set 454 of wells 452.

In some embodiments, systems capable of mechanically stressing the cellular material grown in a bioreactor are desirable. Natural bone and cartilage growth is known to be affected by mechanical stresses encountered by those tissues as they grow, thus systems allowing the introduction of such stresses can facilitate tissue growth which more accurately resembles native tissue growth. Accordingly, FIGS. 8-11 illustrate several systems capable of mechanically stressing tissues as they grow in a bioreactor such as the bioreactor 100 described above.

Figure 8:
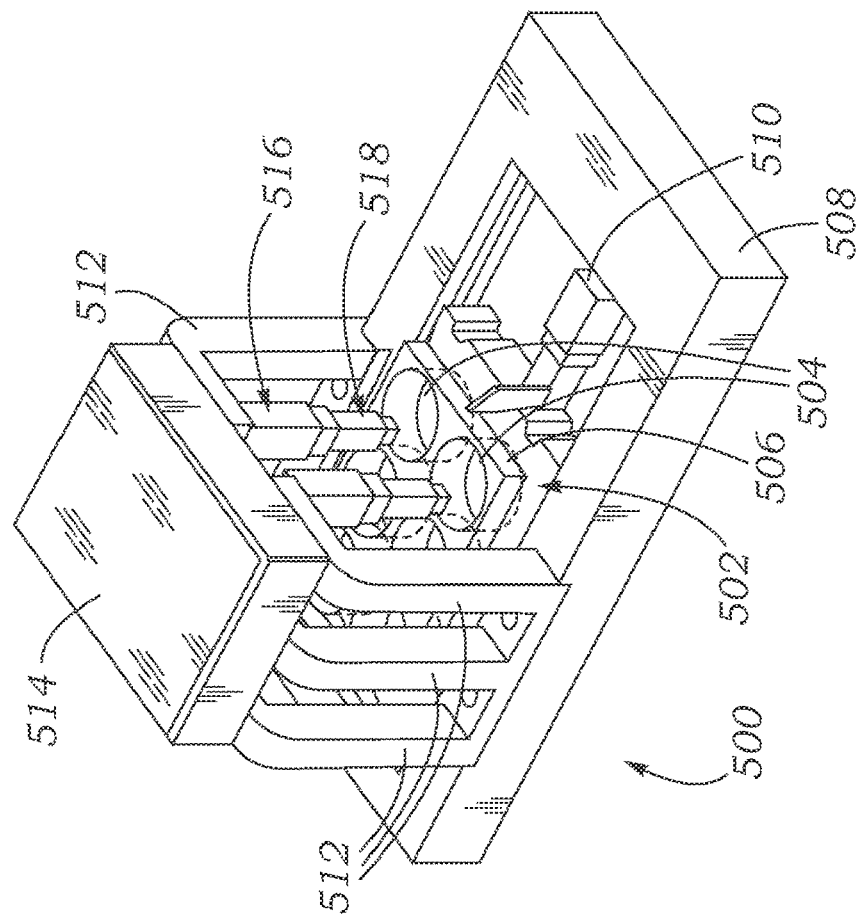
FIG. 8 shows a schematic drawing of an exemplary system having a plurality of mechanical actuators capable of mechanically stressing tissues within bioreactors or laboratory plates.

FIG. 8 shows an exemplary system 500 comprising an array 502 of six bioreactors 504, which can have various configurations but in one specific embodiment can be similar to the bioreactor 100. The array 502 can be situated on a mount 506 which can be horizontally slidable relative to a base plate 508. The mount 506 can be actuated to move horizontally relative to the base plate 508 using a sliding actuator 510. The system 500 also includes a set of vertical extension arms 512 rigidly coupled to the base plate 508, and an actuator housing 514 rigidly coupled to the extension arms 512. The actuator housing 514 houses six micromechanical actuators 516, which can be used to impart forces to the bioreactors 504. The actuators 516 can also include force sensors 518 to monitor the force being imparted to ensure that sufficient, but not excessive, force is imparted to the bioreactors 504 and the tissues grown therein.

The system 500 can be modified to allow the six actuators 516 to mechanically stress more than six bioreactors 504. For example, additional bioreactors 504 can be situated on the mount 506 and can be moved under the actuators 516 by action of the sliding actuator 510. Thus, the actuators 516 can be used to sequentially stress tissues in a larger number of bioreactors. In other embodiments, a second sliding actuator can be used to make the mount 506 slidable along two perpendicular axes. Thus, the actuators 116 can be used to induce stresses in tissues in bioreactors of an array having a larger number of bioreactors 504 in two dimensions.

FIG. 8A illustrates an exemplary method in which a multi-well tray of bioreactors can be sequentially stressed with loading forces in groups. For example, the tray 520 contains 24 bioreactors in a 4-by-6 array of wells 522. A mechanical loading apparatus, similar to that described in FIG. 8, can apply loading forces to groups of six of the bioreactors at a time. An exemplary group of six is represented by the six dots 524. After providing loading forces on the group of six represented by the dots 524, the tray 520 and/or the loading mechanism can be shifted such that a different group of six wells 522 and bioreactors is positioned below the six loading members of the loading mechanism. This can be repeated until all 24 bioreactors are imparted with loading forces. In this way, the total of 24 bioreactors can be imparted with loads in four sessions, with six bioreactors being imparted with loading forces in each of the four sessions. FIG. 8A illustrates just one exemplary loading pattern. In other loading patterns, groups of different numbers and/or arrangements of bioreactors can be included in each loading session.

Figure 9:
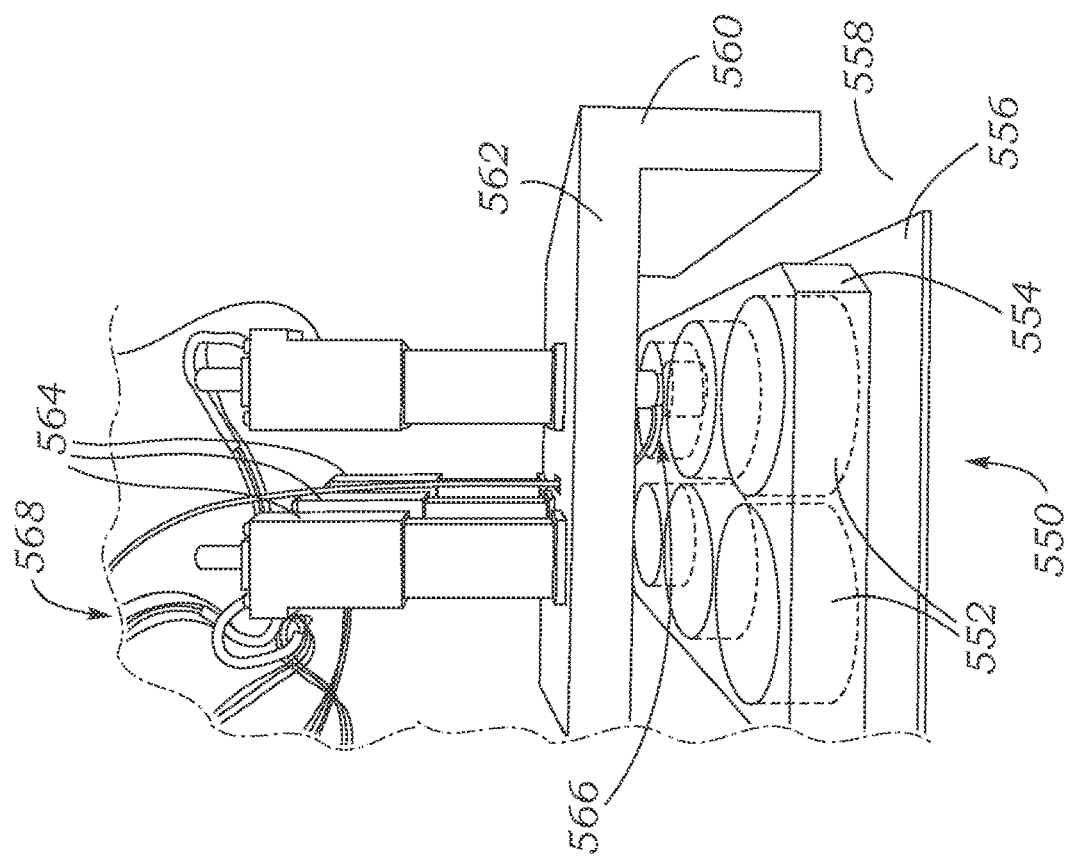
FIG. 9 shows a photograph of another exemplary system having a plurality of mechanical actuators capable of mechanically activating/stressing tissues grown in bioreactors and measuring their mechanical properties.

FIG. 9 shows a side view of an exemplary system 550 comprising six bioreactors 552 housed in a container 554, the container 554 situated on a tray 556 resting on a rigid surface 558. FIG. 9 also shows that supports 560, resting on the rigid surface 558, support an actuator support platform 562, on which six micromechanical actuators 564 are mounted. As in system 500, system 550 can be used to mechanically stress tissues grown in the six bioreactors 552 situated below the actuators 564. As in system 500, force sensors 566 can be coupled to the actuators 564 to measure the forces imparted by the actuators, to ensure sufficient, but not excessive, force is imparted to the tissues in the bioreactors 552. Wiring 568 can be used to couple the actuators to a controller unit such as a computer (not shown). The controller unit can be used to control the forces exerted by the actuators and to monitor force readings from the force sensors 566.

Figure 10:
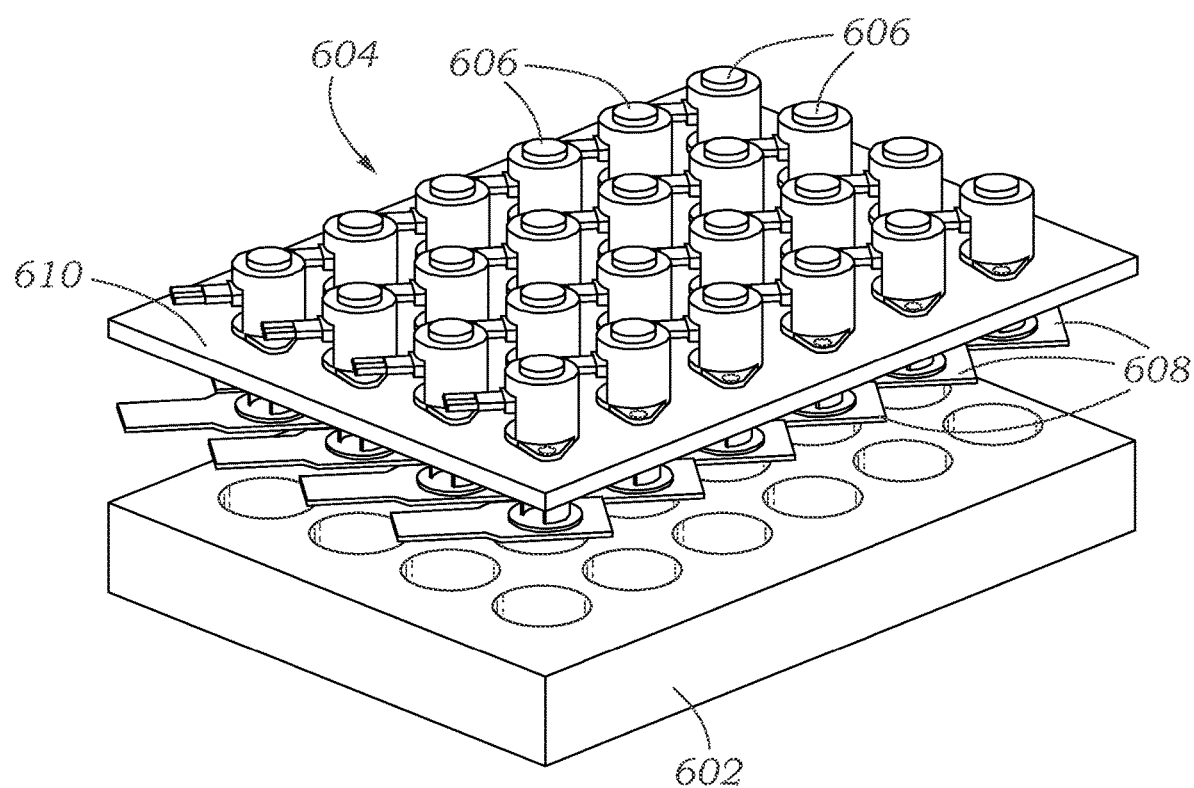
FIG. 10 shows a schematic drawing of another exemplary system having a plurality of mechanical actuators capable of mechanically activating/stressing tissues within laboratory multiwell plates and measuring their mechanical properties.

FIG. 10 shows another exemplary system 600 including a twenty-four well plate 602 and a mechanical stimulator lid assembly 604. The well plate 602 comprises twenty four wells, within each of which a bioreactor (e.g., bioreactor 100) can be situated. An inner body (e.g., an inner body similar to inner body 116) having a protruding ring and being configured to be situated within a well of the well plate 602 can have at least one vertical channel formed in its protruding ring, which channel can be configured to accommodate a pipe or tube which can carry fluid from the lower chamber of a first bioreactor, over the wall between adjacent wells of the well plate 602, and to the lower chamber of a second bioreactor adjacent to the first bioreactor. The mechanical stimulator lid assembly 604 comprises twenty-four micromechanical actuators 606 and twenty-four respective force sensors 608 with associated pistons. The actuators 606 and the sensors 608 are mounted on a support plate 610. As in previous embodiments, the actuators 606 can be used to mechanically stress tissue growing in bioreactors situated in the wells of the well plate 602.

Figure 11:
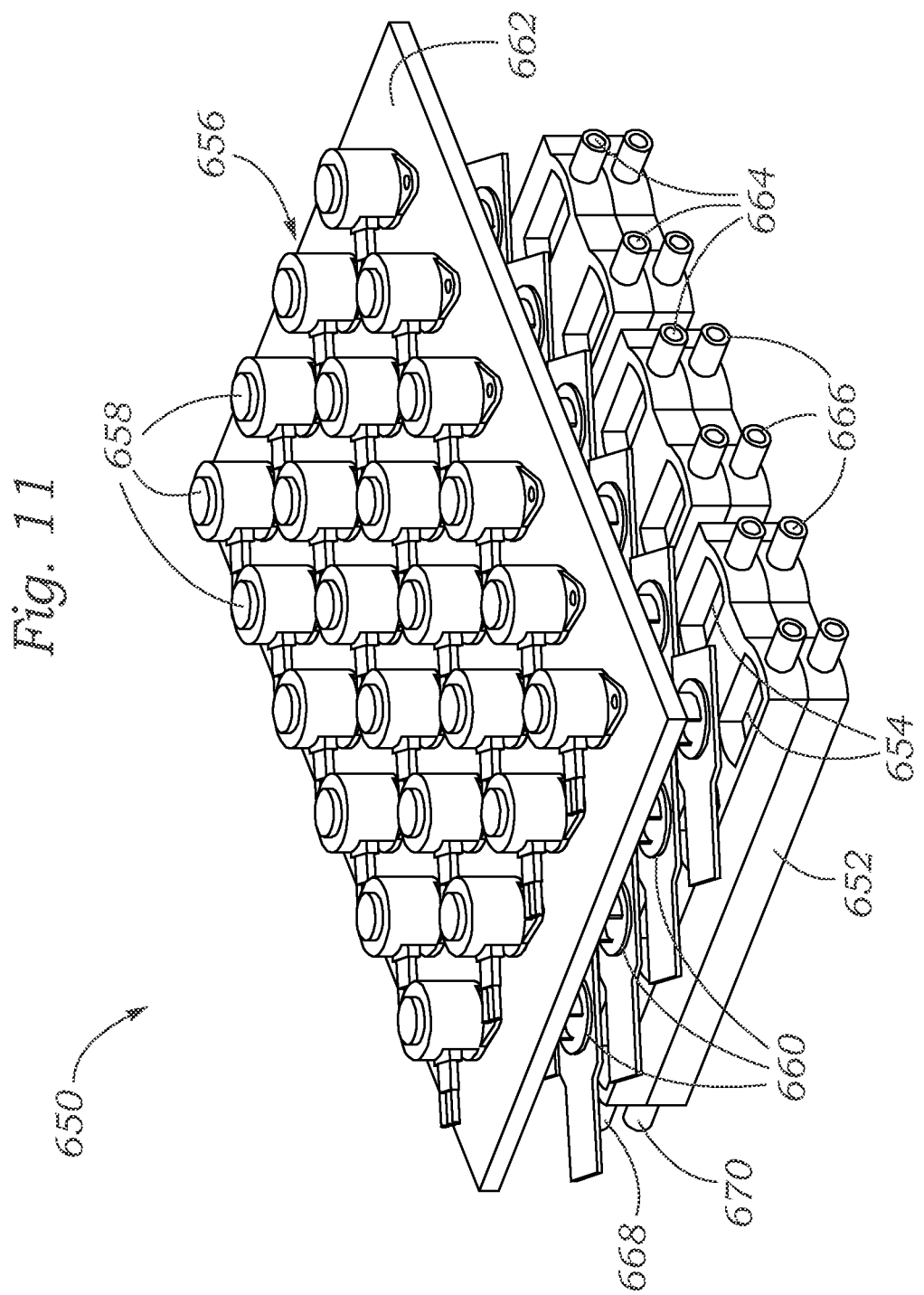
FIG. 11 shows a schematic drawing of another exemplary system having a plurality of mechanical actuators capable of mechanically activating/stressing tissues within bioreactors and measuring their mechanical properties.

FIG. 11 shows another exemplary system 650 similar to system 600. System 650 includes a twenty four well plate 652 comprising twenty-four wells 654, and a mechanical stimulator lid assembly 656 comprising twenty four micromechanical actuators 658 and twenty-four force sensors 660 mounted on a support plate 662. Additionally, FIG. 11 shows upper inlets 664, lower inlets 666, upper outlet 668, and lower outlet 670.

In some embodiments, mechanical actuation or perturbation of tissues in a bioreactor, as described herein, can comprise a "gentle" application of load, for instance <10% strain for 1 hour a day, that mimics the general mechanical environment of the joints without causing damage, and it generally promotes the production and maintenance of better tissue. In other embodiments, mechanical actuation or perturbation can comprise >10% strain that can induce a response similar to an injury response.

The devices, systems, and techniques so far described can be used to facilitate the growth of different tissues, such as tissue found in an organ, for example, an osteochondral microtissue construct from bone. The proposed construct (shown for example in FIG. 1) involves a layered osteochondral tissue composite including, from bottom to top: bone, osteochondral interface, cartilage, and synovium, cultured within a perfusion-ready container mold. As described above, the bone construct can be peripherally surrounded by endothelium to simulate the biological effects of blood vessels and the vasculature on OA. The endothelium can in some cases extend from its location shown in FIG. 1 to form capillary-like structures within the osteoblast construct. Culture-expanded human vascular endothelial cells can be used to form the endothelial lining. The cartilage construct can in some cases also be peripherally surrounded by endothelium, or, as shown in FIG. 1, can be surrounded by human fibroblast (hf) material. Such a layer of hf material can help to simulate interstitial cellular material present in many tissues, for example, the inner lining of the synovial cavity.

Endothelial cells release factors such as fibroblast growth factors (FGFs), interleukin-1β (IL-1β), and interleukin-6 (IL-6), and nitric oxide (NO) which influence both bone and osteoclast behavior, thereby regulating bone formation and resorption. In particular, endothelial cells provide a robust source of bone morphogenetic protein-2 (BMP-2) which enhances the osteogenic phenotype in bone and bone-progenitor cells. In turn, endothelial cells are the target of many bone-derived signals, such as parathyroid hormone (PTH), insulin-like growth factors types 1 and 2 (IGF-1 and IGF-2), basic fibroblast growth factor (bFGF), platelet derived growth factor (PDGF), and vascular endothelial cell growth factor (VEGF).

Each type of tissue used in the devices, systems, and methods described herein can be formulated with the use of scaffold crosslinking technologies, such as projection stereolithography (PSL) to incorporate internal 3D spatial features which permit optimal tissue formation and medium perfusion. For example, 500-micron-diameter channels can be fabricated within the bone construct to aid in nutrient dispersion throughout the construct. Bone can be formed by seeding and culturing MSCs in photocrosslinked collagen/hydroxyapatite. Collagen and hydroxyapatite, or $Ca_{10}(PO_4)_6(OH)_2$, are primary components of bone, and both are frequently used in tissue engineered bone constructs. Cartilage can be engineered by seeding MSCs in a photo-activated/crosslinked polymeric gel, such as a collagen/chitosan gel, and treated with TGF-β3. Chitosan can be advantageous, as it shares some structural characteristics with glycosaminoglycans, a critical component of cartilage responsible for many of its specific mechanical properties. With its many primary amine groups, chitosan can also aid in collagen crosslinking.

Osteochondral interfaces can be formed from a variety of cellular and other materials arranged in various combinations with one another. An exemplary osteochondral interface can be formed by placing a layer of MSC-laden collagen type I hydrogel between the chondral and osseous layers. The synovial lining can be generated with MSCs seeded in crosslinked polyethylene glycol alone and cultured in non-inductive medium. These conditions have been shown in preliminary experiments to be capable of maintaining a fibroblastic phenotype in MSCs. As previously mentioned, the endothelial component can comprise endothelial cells embedded in collagen to surround the osteochondral elements. Collagen gels can be selected based on their susceptibility to modification and contraction by endothelial cells and osteoblasts, which can result in a tight fit around the osteoblast construct.

As there are limited differentiated cell sources available for cartilage and bone tissue engineering, adult multipotent mesenchymal stem cells (MSCs), with their well-characterized ability to differentiate into chondrocyte- and osteoblast-like cells, represent an advantageous candidate cell source for engineering these tissues. Human MSCs derived from bone marrow or from adipose (lipoaspirate) can be used as the progenitor cell population to engineer the bone, cartilage, and synovium components of the microtissue. However, the microtissue system described herein is compatible with constructs derived from any type of progenitor or primary cell. Indeed, induced pluripotent stem cells, with their ability to be propagated to meet the high cell requirements of tissue engineering, represent an attractive, high-quality cell source and provide one exemplary alternative source.

Bioreactor designs can include two separate circulating feeding/delivery systems, such as those shown in FIG. 1 including lower chambers 128, 130 and upper chambers 132, 134, which may be mixed if desired. A first system (e.g., chambers 132, 134) can supply an upper "synovial compartment" and can be separated by an upper screen (such as upper porous screen 126) having 20 µm pores, which in some cases can include a 0.2 µm filter lining. An outer surface of the upper screen can be layered with endothelial cells which adhere thereto and develop after the cells are delivered by perfusion once the construct is assembled. The inner surface of the screen can be lined with a collar of MSC-embedded photo-polymerized hydrogel to constitute the synovium. A second system (e.g., chambers 128 and 130) can supply the bony tissue construct and can be separated from the bone with a rigid wall (e.g., lower porous screen 124) with ≥20 µm pores, thus delivering nutrients as well as allowing endothelial cells and other cells to adhere to and migrate into the bony tissue and create new biologically relevant niches.

As described above, bioreactor systems can include mechanical loading mechanisms. In one exemplary design, the loading device includes a 3 mm loading surface having an unloaded position <0.5 mm from the cartilage surface, and is configured for loading of 5% strain (100 µm) at 0.1 Hz. Reports in the literature suggest that this combination of strain and loading rate should be chondro-stimulatory in engineered cartilage constructs. Furthermore, extreme loading can be applied in conjunction with stimulation by biochemical stresses to simulate physical injury within the microtissue system. In alternative embodiments, the mechanical loading can be force- or stress-driven rather than strain-driven.

One aspect of the microtissue described herein is its ability to mimic the tissue relationships within the osteochondral complex of the articular joint and to characterize responses to mechanical, toxicological, pathological and inflammatory insults or perturbations. The application of the devices, systems, and methods described herein toward these types of studies can proceed according to several steps. First, behavior of the microtissue grown using the devices, systems and methods described herein can be validated under non-stressed conditions to confirm proper matrix production, differentiation marker expression, and tide mark development. Second, the system can be perturbed with mechanical, chemical, and/or toxicological stresses, insults, or perturbations to demonstrate that the microtissue responds according to published in vivo studies.

Third, once validated, the system can be used to investigate biological process not easily studied by traditional means. For example, to study the effects of mechanical injury, the cartilage component can be pre-injured prior to microtissue assembly to study the effects of damaged cartilage on bone health. Alternatively, the assembled and matured microtissue can be impacted to study changes in cartilage and bone anabolic/catabolic pathways and disruption of the tidemark. Similarly, the microtissue system can be employed as a high-throughput in-vitro model to assess the effects of treatment with glucocorticoids, pro-inflammatory cytokines, anti-inflammatory biologics, even biomaterial wear debris, such as titanium and polyethylene microparticles, on osteochondral health. Microtissue systems grown using the devices, systems, and methods described herein offer novel capabilities for investigating the pathogenic mechanisms of OA as well as serving as a high-throughput platform to test candidate DMOADs.

In some methods for developing functional endochondral microtissue, the components of a bioreactor platform (such as including a shell, inner body, upper ring, and other components, similar to those of bioreactor 100) can initially be fabricated, and then the platform design and integrity can be verified using, e.g., structural and media (pH, oxygen, etc.) tests.

In some methods, undifferentiated MSCs can initially be isolated, and then some of them can be pre-differentiated into osteoblasts and chondrocytes. MSC differentiation can then be verified using, e.g., histological and reverse transcription polymerase chain reaction ("RT-PCR") techniques. In some embodiments, undifferentiated MSCs can be encapsulated in a collagen type 1 gel to form a mesenchymal construct. Undifferentiated MSCs can also be encapsulated in PEG to form a synovium. Pre-differentiated osteoblasts can be encapsulated in hydroxyapatite-containing collagen type 1 gel to form an osteoblast construct. Pre-differentiated chondrocytes can be encapsulated in a collagen type 1/chitosan gel to form a chondrocyte construct. Separately, endothelial cells can be isolated and encapsulated in a collagen type 1 gel to form an endothelium. While specific examples of suitable gel matrices are provided herein for exemplary purposes, various other suitable gels are available for use with the various cellular materials. In some embodiments, biological tissues can be used as an alternative to gel matrices for suspending the cellular material.

The various microtissue cellular components thus formed (e.g., mesenchymal construct, synovium, osteoblast construct, chondrocyte construct, and endothelium) can then be verified for viability and tissue type, using, e.g., 3-(4,5-dimethylthiazol-2-yl)-5-(3-carboxymethoxyphenyl)-2-(4-sulfophenyl)-2H-tetrazolium ("MTS"), Live/Dead staining, and/or histology/immunohistochemistry ("IHC") techniques.

The components of a fabricated bioreactor platform can then be combined with these and/or other microtissue cellular components to assemble a bioreactor similar to bioreactor 100. Performance of the microtissues in the bioreactor can then be verified using, e.g., leakage tests, micro computed tomography ("mCT"), magnetic resonance imaging ("MRI"), MTS, Live/Dead, imaging, and/or histology/IHC techniques.

In some embodiments, a mechanical loading system can be provided that is configured to provide a physiological load to the tissue in the bioreactor. Such a loading system can then be verified using, e.g., mCT, MRI, histology/IHC, or imaging techniques.

In some embodiments, the microtissues in a bioreactor can be treated with various insults, such as mechanical, chemical, toxicological, and/or biological insults or perturbations. For example, the microtissue can be mechanically injured by providing a pathogenic load, and the microtissue response can then be measured. As another example, bone pathology can be investigated by treating an osteoblast construct with glucocorticoids and measuring the microtissue response. As yet another example, bone inflammation can be investigated by treating an osteoblast construct with pro-inflammatory cytokines (e.g., TNF-$\alpha$, etc.) and measuring the microtissue response. As another example, bone exposure to particulates can be investigated by treating an osteoblast construct with titanium microparticles and measuring the microtissue response. As another example, the microtissues can be exposed to any of various implant wear debris, such as microparticles of ultra-high-molecular-weight polyethylene (UHMWPE), titanium, chromium/cobalt, etc., and the microtissue response can be measured. As another example, the microtissues can be exposed to various cells, such as cells typical of an inflammatory environment, and the microtissue response can be measured. In each of these examples, the microtissue response can be measured using, e.g., ELISA, imaging, histology/IHC, mCT, MRI, or matrix metalloproteinases ("MMP") activity techniques.

In some embodiments, cartilage health can be tracked based on gene expression activities, e.g., using adeno-associated virus (AAV)-based tissue-specific promoter-reporter constructs.

While portions of the present disclosure have been directed to the growth and study of bone and cartilage tissues, the devices, systems, and methods disclosed herein are applicable to various other biological tissues and structures. For example, the bioreactors and methods described herein can be used to facilitate the growth and/or study of any set of tissues, particularly a set of tissues in which interactions between the different tissues are suspected or known to exist and are a target for study. For example, a single layer of tissue or combinations of two, or three, or four, or five, or more layers of different tissues can be studied using the devices, systems, and methods disclosed herein. Specific examples include an osteochondral complex and chondrocyte complex without a mesenchymal complex, and various other examples provided above.

Further, either as a substitute for or in addition to an MSC layer, in some cases, a membrane having any of various suitable pore sizes can be situated between any of various tissue layers being cultured in a bioreactor. For example, the membrane could take the place of an MSC layer as described above. Further, except where structurally impossible, any of the devices, systems, and components thereof described herein can be used in any of various suitable combinations with one another. For example, any of the inserts (e.g., as shown in FIGS. 5A-B) described herein can be used in combination with any of the fluidic systems (e.g., well plates) described herein, and/or in combination with any of the perturbation sources (e.g., mechanical actuators, chemical perturbations, or toxicological perturbations) described herein. Further, any of the dimensions of such devices and components thereof can be modified to accommodate other components and devices.

In some embodiments, bioreactors and associate components, as described herein, can comprise materials that are transparent to X rays so that it is possible to image by microCT the construct within the bioreactor. Similarly, the bioreactor materials can be such that other imaging techniques, such as fluorescence microscopy, can be used "non-invasively," without removing the constructs from the bioreactor.

Example 1

To evaluate some of the devices, systems, methods, and techniques described herein, studies were conducted. Tissue engineering (TE) bone was formed by seeding human MSCs ($4\text{-}20\times10^6$/ml) in gelatin/hydroxyapatite hydrogels by photocrosslinking, and cultured in BMP-2 included osteogenic media. Cartilage was engineered by seeding MSCs ($4\text{-}60\times10^6$/ml) in gelatin/hyaluronic acid hydrogel by photocrosslinking, and treated with transforming growth factor-$\beta3$ (TGF-$\beta3$) included chondrogenic medium. Osteochondral interfaces were formed by placing layers of MSC-laden ($4\text{-}20\times10^6$/ml) gelatin hydrogels between the chondral and osseous-constructs. This 3-layer TE osteochondral tissue was then inserted into the mold shown in FIGS. 5C and 5D and cultured in a chamber as shown in FIG. 6 with 2 separated fluid streams for 6 weeks. The upper fluid stream 384 supplied chondrogenic medium (CM) and the lower fluid stream 386 supplied osteogenic medium (OM) at a flow rate of 1 µl/s. [CM: Dulbecco's Modified Eagle's Medium (DMEM) supplemented with 10 ng/ml recombinant human TGF-$\beta3$ (Peprotech), 1% Insulin-Transferrin-Selenium, 50 µM ascorbic acid 2-phosphate, 55 µM sodium pyruvate, 23 µM L-proline, and 1% antibiotics-antimycotic. OM: $\alpha$-MEM containing 10% fetal bovine serum, 1% antibiotics-antimycotic, 10 ng/ml recombinant human bone morphogenetic protein-2 (BMP-2; PeproTech), 1% L-alanyl-L-glutamine, 10 nM dexamethasone, 0.1 mM L-ascorbic acid 2-phosphate, and 10 mM $\beta$-glycerophosphate].

Next, a native bone and endothelial cell construct was prepared. The microvascular endothelial cell (EC) line HMEC-1 was maintained in EGM-2MV media (Lonza). Human bone plugs were harvested from human trabecular bone using 5.0 mm diameter biopsy hole punches (Miltex) and cultured in DMEM/10% FBS/1% PS for two weeks. EC-containing collagen gels were prepared using the 3D Collagen Culture Kit (Millipore) according to the manufacturer's instructions. Briefly, ice-cold 0.4 ml collagen solution was mixed with 0.1 ml 5×M199 medium and 12.5 µl neutralization solution in 1.5 ml Eppendorf tubes. 25 µl of EC solution ($40\times10^6$ cells/ml DMEM) was added and mixed thoroughly. Bone plugs were then coated in EC/collagen gel by immersion in gel solution for 1 hour in a cell culture incubator. Native bone-EC constructs were cultured in 24-well plates containing 1 ml DMEM/10% FBS/1% PS per well for 0, 4, or 6 weeks.

Next, an osteoprotegerin enzyme-linked immunosorbent assay (ELISA) was performed. Native bone-EC constructs were washed in PBS and cultured in serum-free media for 4 days. Conditioned media samples were collected and analyzed by osteoprotegerin ELISAs (Abcam) exactly according to the manufacturer's instructions.

Next, histology and immunohistochemistry (IHC) was performed. TE bone-cartilage constructs and native bone-EC constructs were washed in PBS and fixed in 4% paraformaldehyde (Electron Microscopy Sciences) overnight at 4° C. Native bone-EC constructs were decalcified overnight in Decal® (Decal Chemical Corporation) at 4° C. To prepare samples for paraffin embedding, constructs were dehydrated by graded ethanol washes (30%, 50%, 70%, 95%, 100%), each overnight at 4° C., cleared in xylene for 1 hour at room temperature, and infiltrated with paraffin wax in 1:1 paraffin:xylene mix for 10 minutes at 60° C. Samples were incubated in 60° C. paraffin overnight to remove residual xylene, embedded, and sectioned (7 µm thickness).

For hematoxylin and eosin staining, samples were washed twice in Histo-Clear II (Electron Microscopy Sciences), rehydrated in graded ethanols (100%, 95%, 70%, 50%) for 1 min each, washed in deionized water for 1 min, stained in Gill No. 2 hematoxylin (Sigma-Aldrich) for 20 min, washed in running tap water for 1 min, immersed in acid alcohol (0.25% HCl in 70% ethanol) and then Scott's tap water substitute (10 g MgSO4, 0.75 g NaHCO$_3$, 1 L ddH2O) for 30 seconds each, washed in running tap water for 2 min, and stained in alcoholic eosin Y 515 (Leica) for 1 min. The samples were then dehydrated in graded ethanols (95%, 100%) for 1 min each, washed twice with Histo-Clear II for 1 min each, mounted with Clarion Mounting Media (Biomeda), and coverslipped.

For IHC, samples were rehydrated via gradient ethanol washes (100%, 95%, 70%, 50%) for 1 min each and washed in running tap water for 5 min. Following antigen retrieval via citrate buffer, pH 6.0 (eBioscience) for 40 min at 90° C., endogenous peroxidase activity was blocked with 3% H2O2 in methanol for 10 min at room temperature. Samples were then incubated with 1% horse serum for 45 min at room temperature and primary antibody (osteoprotegerin (Abcam), osteocalcin (Abcam)) diluted 1:200 with 1% horse serum overnight at 4° C. in humidified chambers. Following washes with PBS, samples were incubated with biotinylated secondary antibody (Vector Labs) for 30 min at RT, washed with PBS, incubated with HRP-conjugated streptavidin (Vector Labs) for 30 min at RT, washed with PBS, incubated with Vector®NovaRed™ peroxidase substrate for 1 min, washed with tap water, counterstained with hematoxylin OS (modified Mayer's formula) (Vector) for 3 seconds, washed in running tap water for 5 min, dehydrated in graded ethanols (95%, 100%) for 5 min each, washed twice in Histo-Clear II for 5 min each, mounted with Clarion Mounting Medium, and coverslipped. Histology and IHC images were captured with an Olympus CKC41 microscope outfitted with a Leica DFC 3200 camera.

FIGS. 12A-B show exemplary resulting osteochondral microtissue constructs, under 10× and 20× magnification, respectively (the bar in the lower corner of each of FIGS. 12A and 12B represents 100 µm). FIGS. 12A-B show, in particular, an interface between an osteoblast construct (labeled oc) and a mesenchymal construct (labeled mc), grown in accordance with the techniques described above, after six weeks of culture. The arrows indicate a dense structure between the two layers.

To evaluate the effects of crosstalk between endothelial cells and bone cells in the disclosed systems, studies were conducted in which native bone plugs were cultured with collagen gels seeded with or without endothelial cells and cultured for four weeks. The results indicate that samples of bone coated with collagen gels containing endothelial cells produce more new bone matrix and osteoprotegerin, indicating activation of anabolic bone pathways. Specifically, FIGS. 13A-B show bone growth in control tests in the absence of endothelial cells, at 10× and 20× magnification, respectively. This can be compared to the results shown in FIGS. 14A-B, which show bone growth in the presence of endothelial cells, at 10× and 20× magnification, respectfully.

Figure 15:
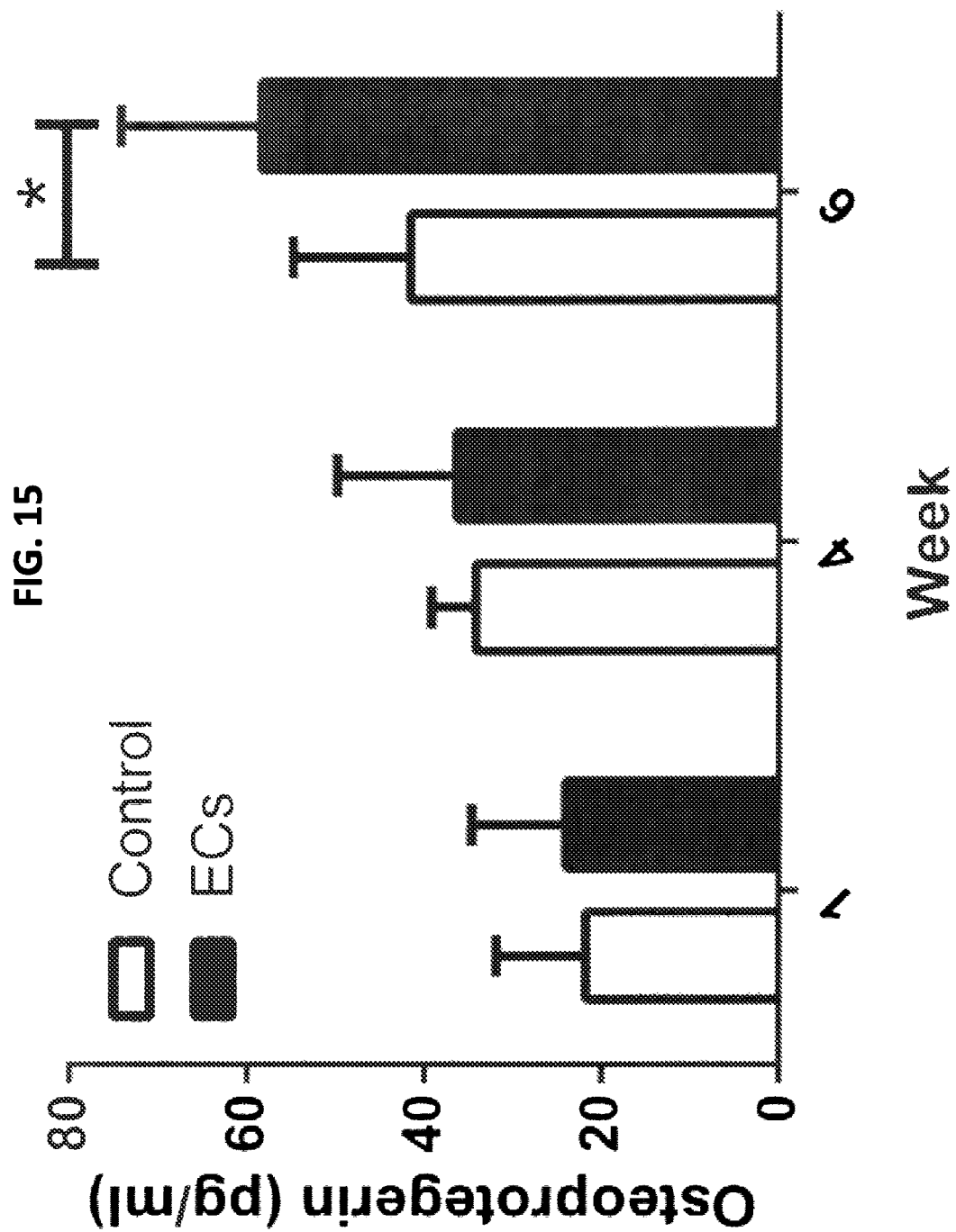
FIG. 15 shows a chart illustrating the behavior of tissues in the presence and in the absence of endothelial cells, at 1 week, 4 weeks, and 6 weeks of growth.

As can be seen, bone growth was greater in the tests in which endothelial cells were present. Future work will assess the extent to which crosstalk with endothelial cells mitigates the negative effects of injurious mechanical and chemical stresses on bone behavior (e.g., by promoting growth, as established by the results shown in FIGS. 13-14). In each of FIGS. 13A, 13B, 14A, and 14B, tissues were IHC-stained for osteoprotegerin, the bar in the lower right corner represents 100 μm, B indicates a bone plug, and G indicates a collagen gel. FIG. 15 shows an ELISA analysis of media samples conditioned by bone plugs coated in collagen gel with and without endothelial cells for 1, 4, and 6 weeks. The asterisk indicates that p=0.0362.

Example 2

The disclosed reactors can achieve cellular communication between the different tissues in the two compartments of the reactor, and each signals to the other in response to changes in the local environment. In a specific example, when bone is stimulated by hormones simulating the menstrual cycle, the hormones initiate an anabolic response and signal to cartilage that will respond even without direct exposure to the hormones. The ability to study this phenomenon is particularly important because hormonal exposure has a protective effect against bone volume loss. To evaluate this effect, a first experiment used a native osteochondral plug.

Figure 16:
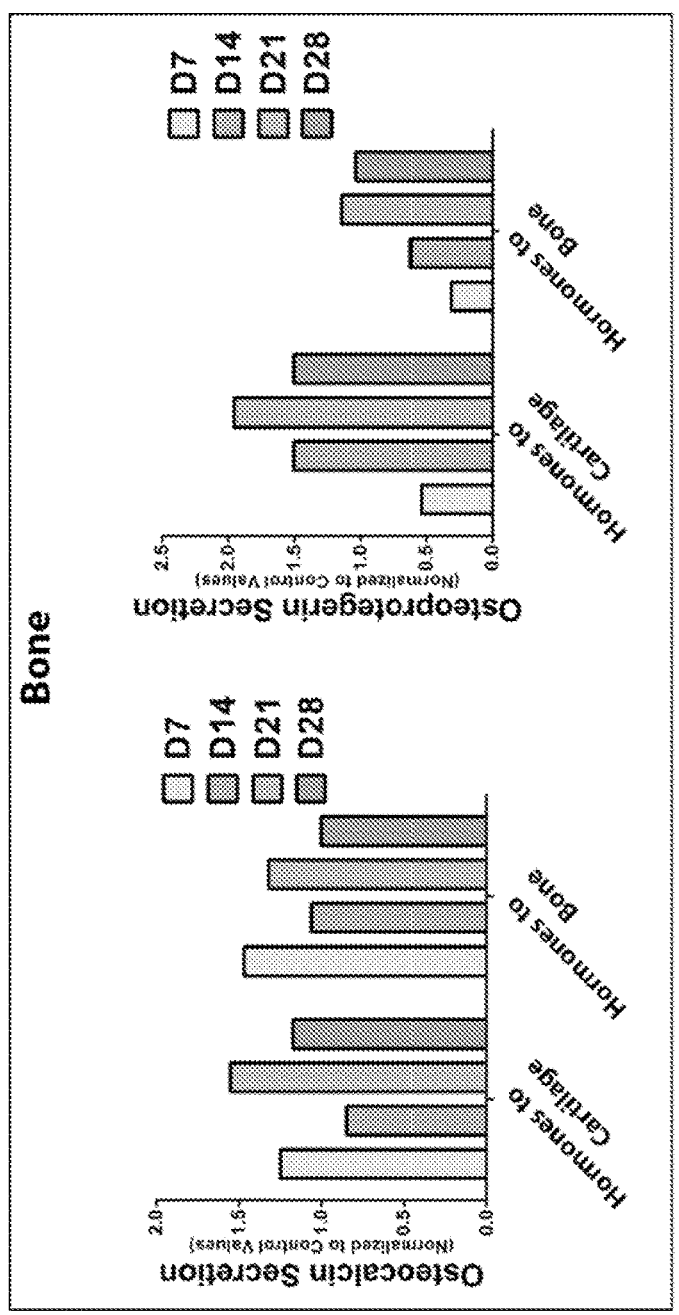
FIG. 16 is a graph showing ELISA data demonstrating use of the bioreactor for evaluating response of cartilage and bone to exposure to hormones. Osteocalcin and osteoprogerin secretion from bone and cartilage is shown at day 7 (D7), day 14 (D14), day 21 (D21), and day 28 (D28).

For the osteochondral plug experiment, human osteochondral plugs from the knees of women undergoing total knee replacement were explanted from macroscopically asymptomatic regions of the joint. Three treatment groups were evaluated with different fluid flow between the top (cartilage) and lower (bone) chambers of the bioreactor. The fluid flows to the top and bottom chambers included Dulbecco's Modified Eagle Media (DMEM), Fetal Bovine serum (FBS), and Penicillin/Streptomycin/Amphotericin (PSF), optionally with hormones that simulate the menstrual cycle. The treatment groups were as follows:

Treatment Groups:
1. Top: DMEM+FBS+PSF
   Bottom: DMEM+FBS+PSF
2. Top: DMEM+FBS+PSF+hormones simulating the menstrual cycle
   Bottom: DMEM+FBS+PSF
3. Top: DMEM+FBS+PSF
   Bottom: DMEM+FBS+PSF+hormones simulating the menstrual cycle For the groups in which hormones were supplied, the media was altered over the time course shown in FIG. 16. The results (FIG. 16) showed that hormones affected both bone and cartilage. In particular, hormone treatment reduced osteocalcin secretion and enhanced osteoprotegerin secretion. The results also provided evidence of a cyclic bone response to changing concentrations of hormones that mimicked changes that would be seen throughout the menstrual cycle of a woman. The hormones prevented loss of calcification in the osteochondral junction.

Example 3

Figure 17:
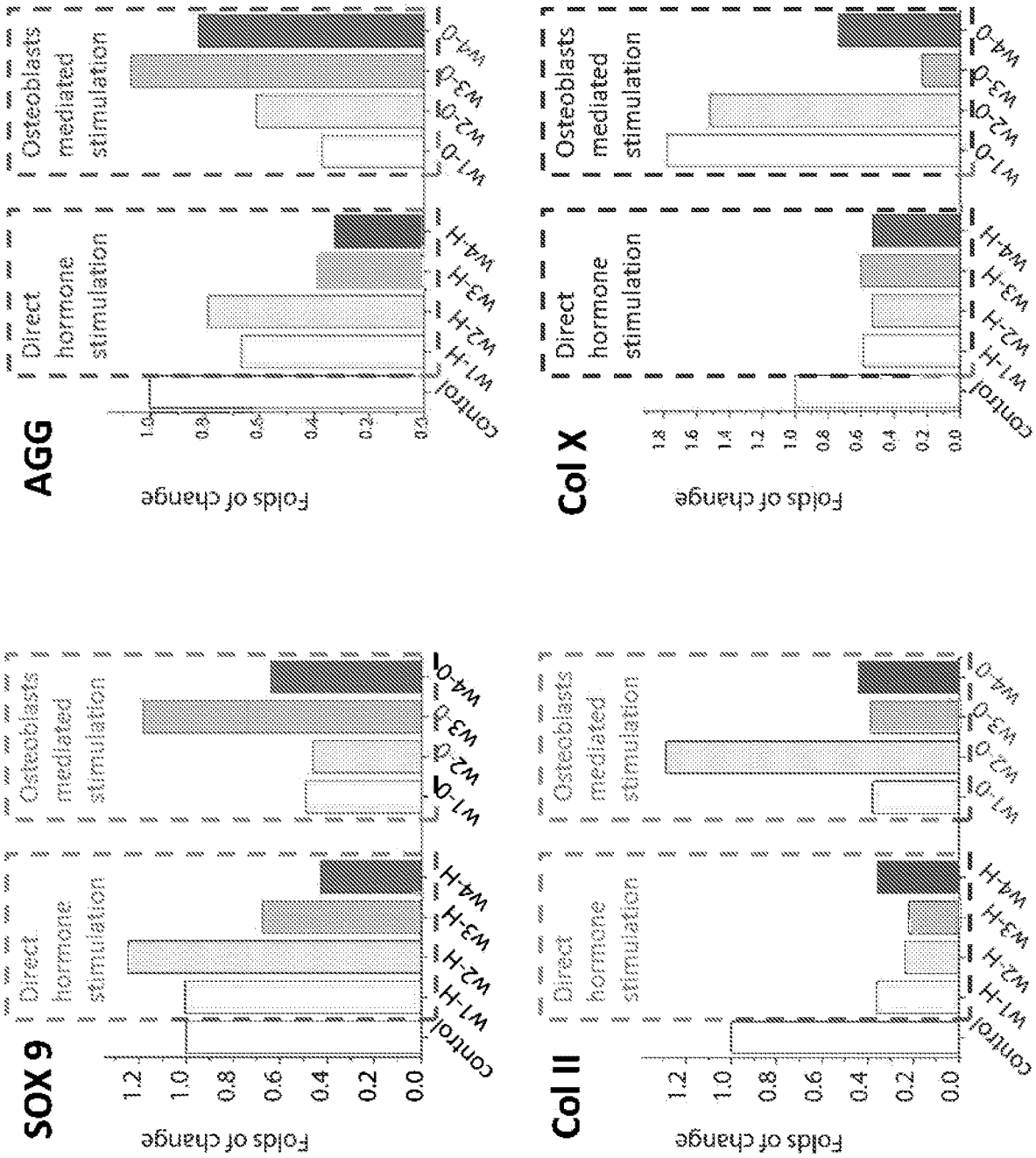
FIGS. 17-20 are graphs that show differential expression of markers (as determined by RT-PCR) for a control medium that contained no estrogen or progesterone (first bar), and then different concentrations of hormones supplied to one or the other of the bioreactor chambers during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone).
Figure 18:
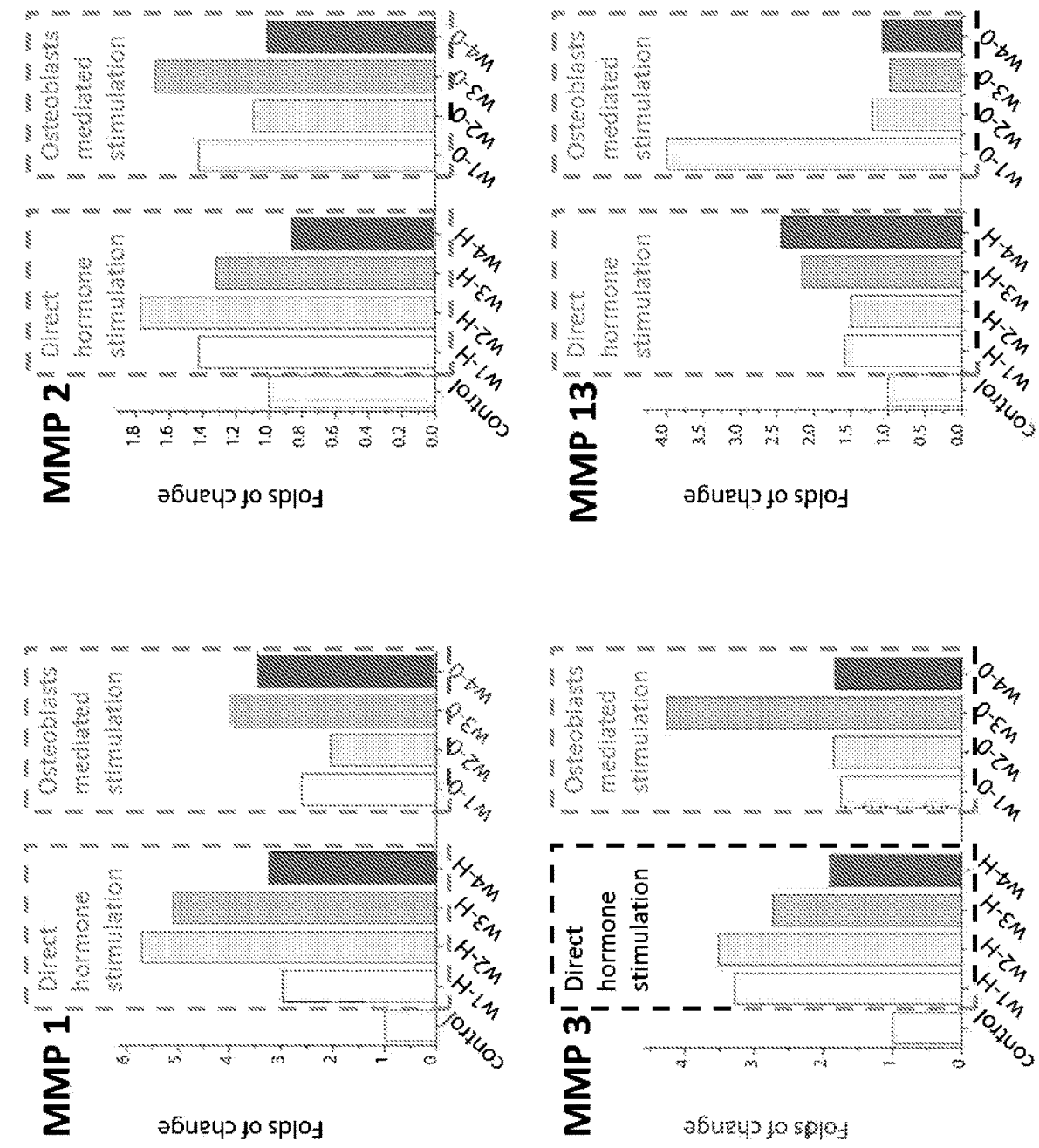

In another demonstration of the use of the bioreactor, a chondrocyte response was shown using real time PCT (RT-PCR) to illustrate that stimulation of bone tissue in the lower chamber of the bioreactor stimulated a chondrocyte response in the upper chamber. FIGS. 17-18 show differential expression of markers (as determined by RT-PCR) for a control medium that contained no estrogen or progesterone (first bar), and then different concentrations of hormones supplied to the chambers during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone). "Direct hormone stimulation" indicates that the hormones were supplied to the cartilage (top) chamber of the bioreactor; "osteoblasts mediated stimulation" indicates that the hormones were supplied to the bone (bottom) chamber of the bioreactor and had an indirect effect on the chondrocytes in the cartilage chamber.

Figure 19:
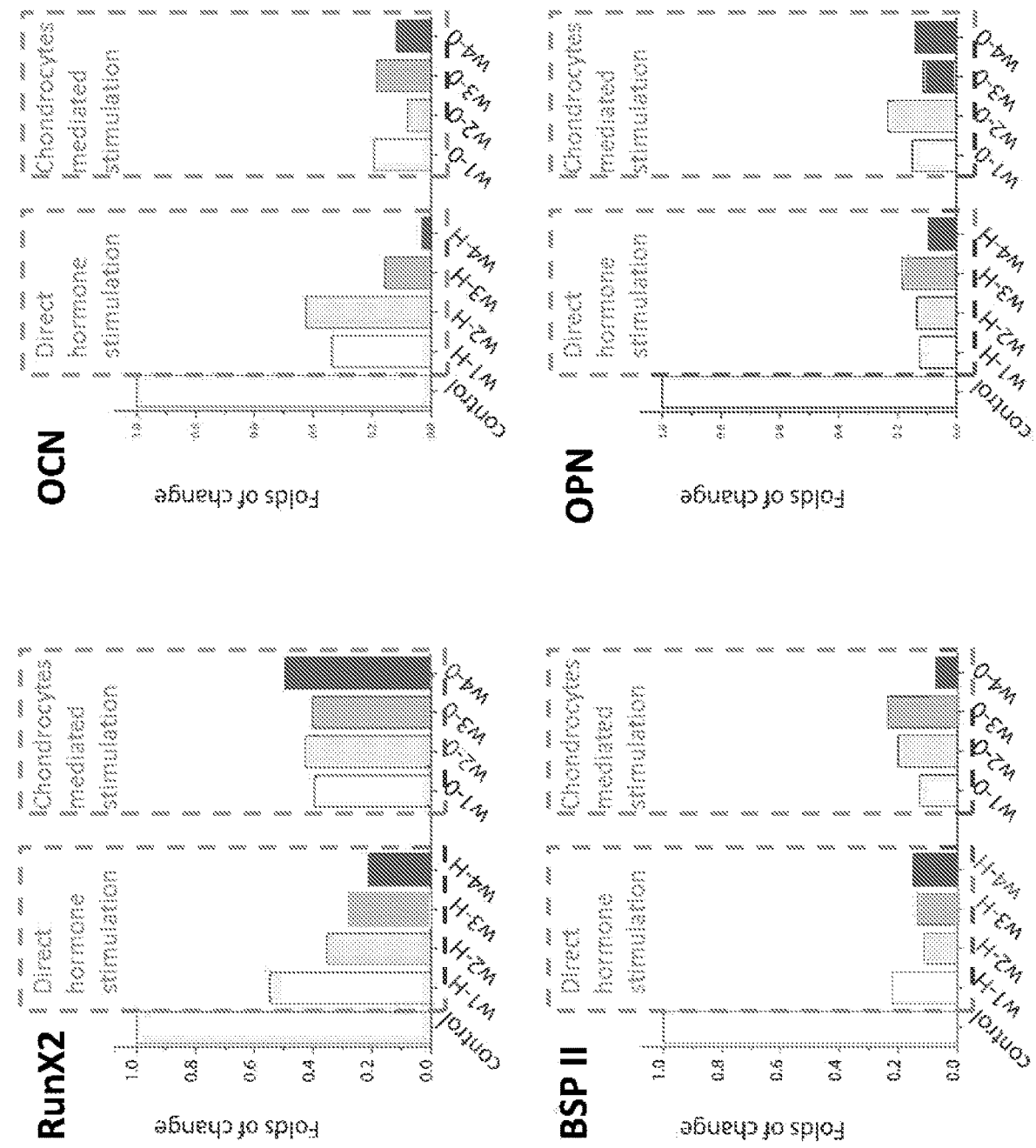
Figure 20:
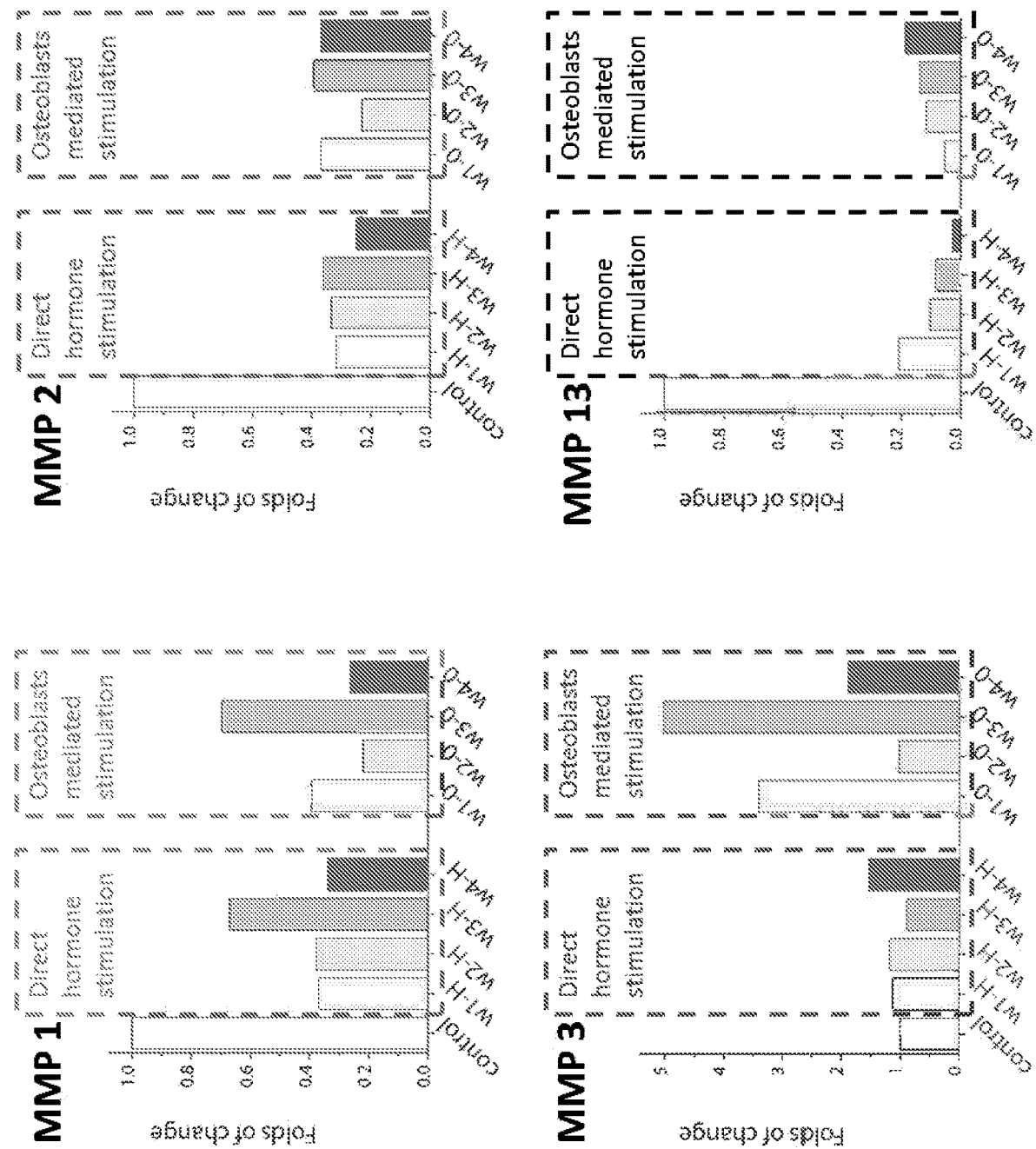

FIGS. 19-20 show differential expression of markers (as determined by RT-PCR) for a control medium that contained no estrogen or progesterone (first bar), and then different concentrations of hormones supplied to the cartilage chamber during week 1 (w1: 0.1 nM estradiol), week 2 (w2: 1 nM estradiol), week 3 (w3: 1 nM estradiol and 10 nM progesterone), and week 4 (w4: 0.1 nM estradiol and 50 nM progesterone). "Direct hormone stimulation" indicates that the hormones were supplied to the bone (bottom) chamber of the bioreactor; "chondrocytes mediated stimulation" indicates that the hormones were supplied to the cartilage (top) chamber of the bioreactor and had an indirect effect on the osteoblasts in the bone chamber.

Higher concentrations of estradiol in the bone chamber of the bioreactor (FIGS. 17-18, weeks 1 and 2) downregulated cartilage anabolic markers such as Sox9 and Aggrecan, but downregulation is more pronounced when estradiol is applied to the osseous side. When progesterone is progressively added (week 3 and 4), downregulation is still present but with an opposite trend (higher when hormones are directly applied to cartilage). Bone anabolic markers are generally downregulated in all conditions. Cartilage hypertrophy marker ColX is upregulated only when estradiol is administered to the osseous side, and downregulated in any other conditions, suggesting a concomitant signaling from osteoblasts. Metalloproteinases are generally upregulated in cartilage for all conditions (except MMP-13 which has a more complex behavior).

As shown in FIGS. 19-20, metalloproteinases are generally downregulated in bone for all conditions (except MMP-3 which has a more complex behavior). Bone anabolic markers are generally downregulated in all conditions.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims. We therefore claim all that comes within the scope and spirit of these claims.

The invention claimed is:

1. A bioreactor comprising:
   a shell having an upper opening and an inner space, the inner space having an inner diameter;
   an upper ring;
   a piston; and
   an inner body situated within the inner space of the shell, wherein the shell is configured such that the inner body is insertable into the inner space through the upper opening, wherein the inner body includes a one-piece tubular body comprising an upper portion having first perforations and defining an inner upper chamber and a lower portion having second perforations and defining an inner lower chamber, the inner body further comprising a protruding ring positioned outside of the tubular body between the upper and lower portions, wherein:
the protruding ring has an outer diameter corresponding to the inner diameter of the shell, such the protruding ring seals against a radially inner surface of the shell when the inner body is inserted into the inner space through the upper opening;
the upper portion of the tubular body has an outer diameter which is smaller than the inner diameter of the shell to create an outer upper chamber between the upper portion of the tubular body, the protruding ring, and the shell, the outer upper chamber being in fluid communication with the inner upper chamber via the perforations in the upper portion of the tubular body; and
the lower portion of the tubular body has an outer diameter which is smaller than the inner diameter of the shell to create an outer lower chamber between the lower portion of the tubular body, the protruding ring, and the shell, the outer lower chamber being in fluid communication with the inner lower chamber via the perforations in the lower portion of the tubular body;
wherein the upper ring is positioned adjacent the upper opening of the shell above the inner body such that the upper ring secures the inner body within the shell, the upper ring having a central aperture for the piston, the central aperture having an inner diameter that is about equal to an inner diameter of the upper portion of the tubular body; and
wherein the piston extends through the central aperture and into the inner upper chamber of the tubular body, such that an interface between the piston with the upper ring and the tubular body forms a seal while allowing the piston to reciprocate relative to the inner body.

2. The bioreactor of claim 1, wherein:
the protruding ring of the inner body seals against an inner surface of the shell, thereby separating the inner space of the shell into the outer lower chamber and the outer upper chamber;
the upper portion is a hollow cylindrical screen separating the outer upper chamber from the inner upper chamber;
the lower portion is a hollow cylindrical screen separating the outer lower chamber from the inner lower chamber; and
the shell includes an upper port allowing access through the shell to the outer upper chamber and a lower port allowing access through the shell to the outer lower chamber.

3. The bioreactor of claim 2, wherein:
the upper port is an upper inlet port and the shell further comprises an upper outlet port allowing access through the shell to the outer upper chamber; and
the lower port is a lower inlet port and the shell further comprises a lower outlet port allowing access through the shell to the outer lower chamber.

4. The bioreactor of claim 3, wherein the bioreactor is a first bioreactor;
the upper inlet port is fed by an upper outlet port of a second bioreactor;
the lower inlet port is fed by a lower outlet port of a second bioreactor;
the upper outlet port feeds an upper inlet port of a third bioreactor; and
the lower outlet port feeds a lower inlet port of a third bioreactor.

5. The bioreactor of claim 4, wherein the shell of the first bioreactor and shells of the second and third bioreactors are all integrated portions of a single multi-well tissue culture plate.

6. The bioreactor of claim 5, wherein the multi-well tissue culture plate is configured to receive the inner body of the first bioreactor and inner bodies of the second and third bioreactors within respective shells of the multi-well tissue culture plate to form the first, second, and third bioreactors.

7. The bioreactor of claim 6, wherein the multi-well tissue culture plate is laterally shiftable relative to at least one mechanical actuator positioned above the single multi-well tissue culture plate to sequentially apply loads to different bioreactors.

8. The bioreactor of claim 2, further comprising biological tissue situated within the inner body.

9. The bioreactor of claim 8, wherein the biological tissue comprises two or more distinct biological tissue layers.

10. The bioreactor of claim 9, wherein a first of the two distinct biological tissue layers is an osteoblast construct and a second of the two distinct biological tissue layers is a chondrocyte construct.

11. The bioreactor of claim 9, wherein one or more of the distinct biological tissue layers comprises two or more types of cells.

12. The bioreactor of claim 1, further comprising a perturbation source that moves the piston relative to the inner body and provides perturbation on tissue contained in the inner body.

13. The bioreactor of claim 12, further comprising a chemical perturbation source.

14. The bioreactor of claim 12, further comprising a toxicological perturbation source.

15. The bioreactor of claim 12, wherein the perturbation source comprises a mechanical driver that couples to the piston to drive the piston in a reciprocal motion.

16. The bioreactor of claim 1, wherein the inner body is configured to contain a first tissue comprising osteoblasts, a second tissue comprising chondrocytes, and an additional tissue layer between the first tissue and the second tissue.

17. The bioreactor of claim 16, wherein the additional tissue layer comprises a mesenchymal stem cell layer situated between the first and second tissues and physically isolating the first and second tissues from one another.

18. The bioreactor of claim 16, wherein the inner body is configured to contain an additional layer comprising synovial cells adjacent to the first tissue.

19. The bioreactor of claim 1, wherein the inner body is configured to contain a layer of cellular material situated on a lateral surface of inner body.

20. The bioreactor of claim 19, wherein the layer of cellular material comprises endothelial cells.

* * * * *